(12) United States Patent
Taguchi

(10) Patent No.: US 6,461,538 B2
(45) Date of Patent: Oct. 8, 2002

(54) PRODUCTION PROCESS FOR INDOLIZINE COMPOUNDS AND THEIR USE IN ORGANIC LIGHT-EMITTING DEVICES

(75) Inventor: Toshiki Taguchi, Kanagawa (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 0 days.

(21) Appl. No.: 09/736,327

(22) Filed: Dec. 15, 2000

(65) Prior Publication Data

US 2001/0015614 A1 Aug. 23, 2001

(30) Foreign Application Priority Data

Dec. 16, 1999 (JP) .......................................... 11-358013
Mar. 28, 2000 (JP) ...................................... 2000/089407
Mar. 31, 2000 (JP) ...................................... 2000/098822

(51) Int. Cl.⁷ ........................ C07D 471/04; C09K 11/02
(52) U.S. Cl. ..................... 252/301.17; 546/112; 546/94
(58) Field of Search ............... 546/112, 94; 252/301.17

(56) References Cited

FOREIGN PATENT DOCUMENTS

JP            311787        11/2000

OTHER PUBLICATIONS

Kido et al, "Bright blue electroluminescence from poly(N–vinylcarbazole)"; *Appl. Phys. Lett.* 63 (19); 1993; pp. 2627–2629.
Tang et al, "Organic electroluminescent diodes"; *Appl. Phys. Lett.* 51 (12) 1987; pp. 913–915.
Adachi et al, "Blue light–emitting organic electroluminescent devices"; *Appl. Phys. Lett.* 56 (9); 1990; pp. 799–801.

*Primary Examiner*—Bernard Dentz
(74) *Attorney, Agent, or Firm*—Burns, Doane, Swecker & Mathis, LLP

(57) ABSTRACT

An organic light-emitting device material is described, comprising at least one compound represented by formula (I) or a precursor thereof:

(I)

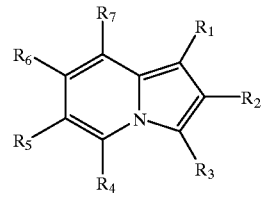

wherein $R_1$ to $R_7$ each independently represents hydrogen atom, a halogen atom, a cyano group, a formyl group or a substituted or unsubstituted alkyl, alkenyl, alkynyl, aryl, heterocyclic, primary, secondary or tertiary amino, imino, alkoxy, aryloxy, alkylthio, arylthio, carbonamido, sulfonamido, carbamoyl, sulfamoyl, alkylcarbonyl, arylcarbonyl, alkylsulfonyl, arylsulfonyl, alkoxycarbonyl, aryloxycarbonyl, alkylcarbonyloxy, arylcarbonyloxy, urethane, ureido or carboxylic acid ester group, two or more groups selected from $R_1$ to $R_7$ may combine with each other to form an aliphatic carbon ring, an aromatic carbon ring, a non-aromatic heterocyclic ring or an aromatic heterocyclic ring and $R_4$ may further represent

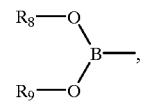

$R_8$ and $R_9$ each represents hydrogen atom, an alkyl group, an aryl group or a heterocyclic group, $R_8$ and $R_9$ may combine with each other to form a cyclic structure or may form a polymer compound having the structure represented by formula (I) in a part of the repeating unit thereof and $R_1$ or $R_3$ in the structure represented by formula (I) and

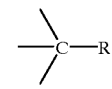

may combine to form a trimer compound, and R represents hydrogen atom, an alkyl group, an aryl group or a heterocyclic group.

5 Claims, No Drawings

PRODUCTION PROCESS FOR INDOLIZINE COMPOUNDS AND THEIR USE IN ORGANIC LIGHT-EMITTING DEVICES

FIELD OF THE INVENTION

The present invention relates to a novel indolizine compound, a method for producing a novel indolizine compound, an organic light-emitting device material having an indolizine skeleton, and an organic light-emitting device using these.

BACKGROUND OF THE INVENTION

At present, studies on and development of various display elements are aggressively proceeding. In particular, organic EL light-emitting devices can afford high luminance emission at a low voltage and is attracting an attention as a promising display device. For example, an EL device comprising an organic thin film formed by depositing an organic compound is known (see, *Applied Physics Letters*, Vol. 51, page 913 (1987)). The organic EL device described in this publication has a laminate structure comprising an electron-transporting material and a hole-transporting material and is greatly improved in the emission properties as compared with conventional single-layer devices.

As concerns the hole-transporting material used in the laminate-type device, triarylamine derivatives including TPD (N,N'-di-m-tolyl-N,N'-diphenylbezidine), and π-electron excess aromatic compounds such as pyrrole, carbazole and thiophene, are known as excellent hole-transporting materials. These π-electron excess aromatic compounds are acknowledged to be effective not only as a hole-transporting material but also as an electron-transporting material, a hole-injecting material or a light-emitting material. However, these compounds have high crystallinity and the organic light-emitting devices using such a compound are known to have a problem in that the device performance is liable to greatly deteriorate during storage, particularly storage at a high temperature.

Triarylamine derivatives are low in the solubility in an organic solvent and these compounds are not suitable for coating-type organic EL devices.

As an electron-transporting material capable of taking the place of the triarylamine derivatives, use of a nitrogen-containing heterocyclic compound such as carbazole derivative is being studied and a large number of cases have been reported on the technique of using a low molecular carbazole derivative or a polyvinyl carbazole as the hole-transporting material, for example, a compound described in *Oyo Butsuri Gakkai Yuki Bunshi Bioelectronics Bunka-kai, Dai 6-kai Koshu-kai Yoko* (1997) (*Society of Applied Physics, Section of Organic Molecules Bioelectronics, 6th Lecture, Preprint*), or the like.

However, as a result of investigations by the present inventors on the compounds such as carbazole derivative, these compounds have a high potential of ionization and have a problem in that an organic EL device capable of emitting light with high efficiency cannot be obtained.

As means for solving the problem of deterioration of the device performance during storage, techniques of, in the case of triarylamine derivatives, introducing a condensed polycyclic aromatic group or using a group of compounds improved in the symmetry property are disclosed in *Appl. Phys. Lett.*, 56, 799 (1990), *Polymer Preprints* (*ACS*), 349 (1997), and the like. Similarly, investigations on nitrogen-containing heterocyclic compounds such as carbazole derivative, and techniques of increasing the molecular weight are disclosed in *Appl. Phys. Lett.*, 63, 2627 (1993).

The present inventors had found that indolizine compounds are effective as the organic light-emitting device material and continuously studied on these compounds. Then, it was found that the indolizine compounds have a problem, similarly to the heterocyclic compounds in series, in that when a compound having a simple structure is used in the organic light-emitting material, a sufficiently high performance cannot be obtained.

Furthermore, in the case of using a known Chichibabin method for synthesizing the indolizine compound, it was difficult to introduce a substituent into various positions of the indolizine mother nucleus. Particularly, in introducing a substituent into the 5-position of the indolizine mother nucleus, when the substituent was introduced into a pyridine ring of the starting material, the synthesis of indolizine mother nucleus encountered great steric hindrance and the mother nucleus was difficult to form. When the substituent was attempted to introduce after the ring formation, the substituent could not be easily introduced into the 5-position because the 1-position and 3-position of the indolizine mother nucleus were extremely high in the reactivity with an electrophilic reacting agent.

In recent years, examples of the metalation reaction at the 5-position of the indolizine mother nucleus are reported in *Tetrahedron Lett.*, 33 (31), 4433–4434 (1992). The present inventors thought that by utilizing this reaction, a substituent may be introduced into the 5-position of the indolizine mother nucleus, and made extensive investigations, as a result, it has been found that an indolizine boronic acid ester is effective.

The present invention has been accomplished as a result of these extensive investigations.

SUMMARY OF THE INVENTION

A first object of the present invention is to develop a heterocyclic compound having a good hole-transporting ability and thereby develop an EL device material suitable for the manufacture of high-luminance organic EL device.

A second object of the present invention is to develop a hole-transporting material capable of exhibiting good film-forming property at the fabrication of a device and imparting high stock storability to the device and in turn develop an EL device material having excellent stock storability.

A third object of the present invention is to develop an EL device material suitable for the manufacture of an organic EL device capable of emitting high-luminance light even in the case of a coating-type device.

A fourth object of the present invention is develop a novel indolizine compound and thereby developing an organic light-emitting material suitable for the manufacture of an organic light-emitting device having high luminance and excellent durability.

A fifth object of the present invention is to find out a novel indolizine compound and a production process therefore and develop an organic light-emitting material suitable for the manufacture of a high-luminance organic light-emitting device.

These objects of the present invention can be attained the following indolizine compound, production process therefor, organic light-emitting device material and organic light-emitting device.

1) An organic light-emitting device material comprising at least one compound represented by formula (I) or a precursor thereof:

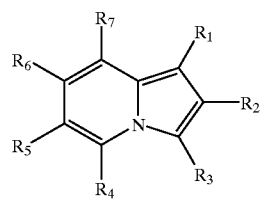
(I)

wherein $R_1$ to $R_7$ each independently represents hydrogen atom, a halogen atom, a cyano group, a formyl group, a substituted or unsubstituted alkyl group, a substituted or unsubstituted alkenyl group, a substituted or unsubstituted alkynyl group, a substituted or unsubstituted aryl group, a substituted or unsubstituted heterocyclic group, a substituted or unsubstituted primary amino group, a substituted or unsubstituted secondary amino group, a substituted or unsubstituted tertiary amino group, a substituted or unsubstituted imino group, a substituted or unsubstituted alkoxy group, a substituted or unsubstituted aryloxy group, a substituted or unsubstituted alkylthio group, a substituted or unsubstituted arylthio group, a substituted or unsubstituted carbonamido group, a substituted or unsubstituted sulfonamido group, a substituted or unsubstituted carbamoyl group, a substituted or unsubstituted sulfamoyl group, a substituted or unsubstituted alkylcarbonyl group, a substituted or unsubstituted arylcarbonyl group, a substituted or unsubstituted alkylsulfonyl group, a substituted or unsubstituted arylsulfonyl group, a substituted or unsubstituted alkoxycarbonyl group, a substituted or unsubstituted aryloxycarbonyl group, a substituted or unsubstituted alkylcarbonyloxy group, a substituted or unsubstituted arylcarbonyloxy group, a substituted or unsubstituted urethane group, a substituted or unsubstituted ureido group or a substituted or unsubstituted carboxylic acid ester group, two or more groups selected from $R_1$ to $R_7$ may combine with each other to form an aliphatic carbon ring, an aromatic carbon ring, a non-aromatic heterocyclic ring or an aromatic heterocyclic ring and $R_4$ may further represent

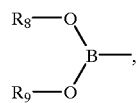

$R_8$ and $R_9$ each represents hydrogen atom, an alkyl group, an aryl group or a heterocyclic group, $R_8$ and $R_9$ may combine with each other to form a cyclic structure or may form a polymer compound having the structure represented by formula (I) in a part of the repeating unit thereof and $R_1$ or $R_3$ in the structure represented by formula (I) and

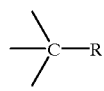

may combine to form a trimer compound, and R represents hydrogen atom, an alkyl group, an aryl group or a heterocyclic group.

2) The organic light-emitting device material as described in 1), which contains a polymer compound derived from a compound containing a polymerizable group in $R_1$ to $R_7$ of formula (I), a trimer compound formed resulting from the combining of $R_1$ or $R_3$ in formula (I) and

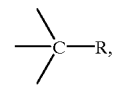

or a compound in which $R_4$ in formula (I) is

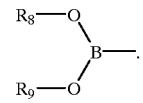

3) A compound represented by the following formula

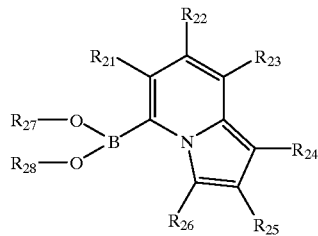
(IV)

wherein $R_{21}$ to $R_{26}$ each independently represents a substituent selected from the group consisting of hydrogen atom, a substituted or unsubstituted alkyl group, a substituted or unsubstituted alkenyl group, a substituted or unsubstituted alkynyl group, a substituted or unsubstituted aryl group, a substituted or unsubstituted heterocyclic group, a substituted or unsubstituted alkoxy group, a substituted or unsubstituted aryloxy group, a substituted or unsubstituted alkylthio group, a substituted or unsubstituted arylthio group, a substituted or unsubstituted alkylamino group, a substituted or unsubstituted arylamino group, a substituted or unsubstituted alkylcarbonyl group, a substituted or unsubstituted arylcarbonyl group, a substituted or unsubstituted alkylsulfonyl group, a substituted or unsubstituted arylsulfonyl group, a substituted or unsubstituted alkoxycarbonyl group, a substituted or unsubstituted aryloxycarbonyl group, a substituted or unsubstituted alkylcarbamoyl group, a substituted or unsubstituted arylcarbamoyl group, a substituted or unsubstituted alkylsulfamoyl group, a substituted or unsubstituted arylsulfamoyl group, a substituted or unsubstituted alkylcarbonyloxy group, a substituted or unsubstituted arylcarbonyloxy group, a substituted or unsubstituted alkylcarbonamido group, a substituted or unsubstituted arylcarbonamido group, a substituted or unsubstituted alkylsulfonamido group, a substituted or unsubstituted arylsulfonamido group, a substituted or unsubstituted urethane group, a substituted or unsubstituted ureido group and a substituted or unsubstituted carbonic acid ester group, the substituents selected from $R_{21}$ to $R_{26}$ may combine with each other to form a cyclic structure, $R_{27}$ and $R_{28}$ each represents hydrogen atom, an alkyl group, an aryl group or a heterocyclic group, and $R_{27}$ and $R_{28}$ may combine with each other to form a cyclic structure.

4) A method for synthesizing a compound represented by formula (IV), comprising metalating an indolizine derivative not having a substituent at the 5-position and then reacting it with a boric acid ester compound.

5) A method for producing a compound represented by the following formula (V), comprising coupling a compound represented by formula (IV) with a vinyl halide, aryl halide or heteroaryl halide compound using a palladium catalyst:

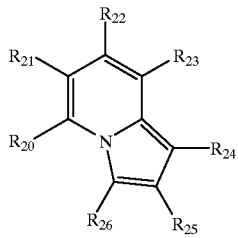

(V)

wherein $R_{20}$ represents an alkenyl group, an aryl group or a heteroaryl group, and $R_{21}$ to $R_{26}$ are the same as the substituent described in formula (IV).

6) An organic light-emitting device having at least one organic light-emitting device material described in 1).

7) The organic light-emitting device as described in 6), wherein at least one organic layer is formed by coating.

DETAILED DESCRIPTION OF THE INVENTION

The compound of the present invention is an indolizine derivative represented by formula (I). The compound of the present invention may be used as an organic light-emitting material in the form of the compound represented by formula (I), or by using a precursor thereof in an organic light-emitting device material, the compound of formula (I) may be derived through a physical or chemical after-treatment during or after the formation of the device.

The compound represented by formula (I) is described in detail below.

$R_1$ to $R_7$ each independently represents hydrogen atom, a halogen atom (e.g., fluorine, chlorine, bromine, iodine), a cyano group, a formyl group, a substituted or unsubstituted alkyl group (preferably having from 1 to 30 carbon atoms, more preferably from 1 to 15 carbon atoms, e.g., methyl, t-butyl, cyclohexyl), a substituted or unsubstituted alkenyl group (preferably having from 2 to 30 carbon atoms, more preferably from 2 to 15 carbon atoms, e.g., vinyl, 1-propenyl, 1-buten-2-yl, cyclohexen-1-yl), a substituted or unsubstituted alkynyl group (preferably having from 2 to 30 carbon atoms, more preferably from 2 to 15 carbon atoms, e.g., ethynyl, 1-propynyl), a substituted or unsubstituted aryl group (preferably having from 6 to 30 carbon atoms, more preferably from 6 to 15 carbon atoms, e.g., phenyl, tolyl, xylyl, naphthyl, biphenyl, pyrenyl), a substituted or unsubstituted heterocyclic group (the heterocyclic ring is preferably a 5- or 6-membered ring and may be condensed with another ring; examples of the heteroatom include nitrogen atom, oxygen atom and sulfur atom; the heterocyclic group preferably has from 2 to 30 carbon atoms, more preferably from 2 to 15 carbon atoms, e.g., pyridyl, piperidyl, oxazolyl, oxadiazolyl, tetrahydrofuryl, thienyl), a substituted or unsubstituted primary, secondary or tertiary amino group (e.g., amino, alkylamino, arylamino, dialkylamino, diarylamino, alkylarylamino, heterocyclic amino, bisheterocyclic amino; preferably a tertiary amino group preferably having from 1 to 30 carbon atoms, more preferably from 1 to 16 carbon atoms, e.g., dimethylamino, diphenylamino, phenylnaphthylamino), a substituted or unsubstituted imino group (a group represented by $-CR_{31}=NR_{32}$ or $-N=CR_{33}R_{34}$, wherein $R_{31}$ to $R_{34}$ each is a group selected from hydrogen atom, an alkyl group, an aryl group, a heterocyclic group, an alkoxy group, an aryloxy group, primary amino group, secondary amino group and tertiary amino group; the imino group preferably has from 1 to 30 carbon atoms, more preferably from 1 to 15 carbon atoms), a substituted or unsubstituted alkoxy group (preferably having from 1 to 30 carbon atoms, more preferably from 1 to 15 carbon atoms, e.g., methoxy, ethoxy, cyclohexyloxy), a substituted or unsubstituted aryloxy group (preferably having from 6 to 30 carbon atoms, more preferably from 6 to 15 carbon atoms, e.g., phenoxy, 1-naphthoxy, 4-phenylphenoxy), a substituted or unsubstituted alkylthio group (preferably having from 1 to 30 carbon atoms, more preferably from 1 to 15 carbon atoms, e.g., methylthio, ethylthio, cyclohexylthio), a substituted or unsubstituted arylthio group (preferably having 6 to 30 carbon atoms, more preferably from 6 to 15 carbon atoms, e.g., phenylthio, tolylthio), a substituted or unsubstituted carbonamido group (preferably having from 1 to 30 carbon atoms, more preferably from 1 to 15 carbon atoms, e.g., acetamido, benzoylamido, N-methylbenzoylamido), a substituted or unsubstituted sulfonamido group (preferably having from 1 to 30 carbon atoms, more preferably from 1 to 15 carbon atoms, e.g., methanesulfonamido, benzenesulfonamido, p-toluenesulfonamido), a substituted or unsubstituted carbamoyl group (preferably having from 1 to 30 carbon atoms, more preferably from 1 to 15 carbon atoms, e.g., unsubstituted carbamoyl, methylcarbamoyl, dimethylcarbamoyl, phenylcarbamoyl, diphenylcarbamoyl, dioctylcarbamoyl), a substituted or unsubstituted sulfamoyl (preferably having from 1 to 30 carbon atoms, more preferably from 1 to 15 carbon atoms, e.g., unsubstituted sulfamoyl, methylsulfamoyl, dimethylsulfamoyl, phenylsulfamoyl, diphenylsulfamoyl, dioctylsulfamoyl), a substituted or unsubstituted alkylcarbonyl group (preferably having from 1 to 30 carbon atoms, more preferably from 1 to 15 carbon atoms, e.g., acetyl, propionyl, butyroyl, lauroyl), a substituted or unsubstituted arylcarbonyl group (preferably having from 6 to 30 carbon atoms, more preferably from 6 to 15 carbon atoms, e.g., benzoyl, naphthoyl), a substituted or unsubstituted alkylsulfonyl group (preferably having from 1 to 30 carbon atoms, more preferably from 1 to 15 carbon atoms, e.g., methanesulfonyl, ethanesulfonyl), a substituted or unsubstituted arylsulfonyl group (preferably having from 6 to 30 carbon atoms, more preferably from 6 to 15 carbon atoms, e.g., benzenesulfonyl, p-toluenesulfonyl, 1-naphthalenesulfonyl), a substituted or unsubstituted alkoxycarbonyl group (preferably having from 1 to 30 carbon atoms, more preferably from 1 to 15 carbon atoms, e.g., methoxycarbonyl, ethoxycarbonyl, butoxycarbonyl), a substituted or unsubstituted aryloxycarbonyl group (preferably having from 6 to 30 carbon atoms, more preferably from 6 to 15 carbon atoms, e.g., phenoxycarbonyl, 1-naphthoxycarbonyl), a substituted or unsubstituted alkylcarbonyloxy group (preferably having from 1 to 30 carbon atoms, more preferably from 1 to 15 carbon atoms, e.g., acetoxy, propionyloxy, butyroyloxy), a substituted or unsubstituted arylcarbonyloxy group (preferably having from 6 to 30 carbon atoms, more preferably from 6 to 15 carbon atoms, e.g., benzoyloxy, 1-naphthoyloxy), a substituted or unsubstituted urethane group (preferably having from 1 to 30 carbon atoms, more preferably from 1 to 15 carbon atoms, e.g., methoxycarbonamido, phenoxycarbonamido, methylaminocarbonamido), a substituted or unsubstituted ureido group (preferably having from 1 to 30 carbon atoms, more preferably from 1 to 15 carbon atoms, e.g., methylaminocarbonamido, dimethylaminocarbonamido, diphenylaminocarbonamido) or a substituted or unsubstituted carbonic acid ester group (preferably having from 1 to 30 carbon atoms, more preferably from 1 to 15 carbon atoms, e.g., methoxycarbonyloxy, phenoxycarbonyloxy).

Two or more groups selected from $R_1$ to $R_7$ may combine with each other to form an aliphatic carbon ring, an aromatic carbon ring, a non-aromatic heterocyclic ring or an aromatic heterocyclic ring.

$R_4$ may represent

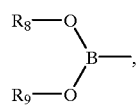

$R_8$ and $R_9$ each represents hydrogen atom, an alkyl group, an aryl group or a heterocyclic group, $R_8$ and $R_9$ may combine with each other to form a cyclic structure.

Furthermore, a polymer compound having a structure represented by formula (I) in a part of the repeating unit may be formed. In this case, it may be possible to contain a polymerizable group such as ethylenically unsaturated bond, or a polymerizable group capable of causing a condensation polymerization, such as carboxyl group, amino group or ester group, in $R_1$ to $R_7$ and form the polymer by the polymerization of the group, or to form the polymer while allowing a precursor of the compound represented by formula (I) to form the skeleton of the compound of formula (I).

In the structure represented by formula (I), $R_1$ or $R_3$ and

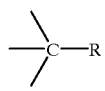

(wherein R represents hydrogen atom, an alkyl group, an aryl group or a heterocyclic group) may combine to form a trimer compound.

The compound represented by formula (I) may be either a low molecule compound or a high molecular compound and the compound which finally works out to the structure capable of exerting the function can be used as it is. The final structure may also be derived from a precursor of the compound by using it in an organic light-emitting device and after or during the fabrication of a device, physically or chemically after-treating the device. In the case of a low molecular compound, the molecular weight is preferably from 200 to 5,000, more preferably from 300 to 2,000. In the case of a high molecular compound, the average molecular weight (Mw) is preferably from 2,000 to 1,000,000, more preferably from 5,000 to 100,000.

Among the above-described atoms and groups represented by $R_1$ to $R_7$, preferred are hydrogen atom, an alkyl group, an aryl group, a heterocyclic group and a tertiary amino group. In the case of a tertiary amino group, the substituent is preferably an aryl group or a heteroaromatic group. In particular, a case where at least one of $R_1$ to $R_3$ is an aryl group or a heteroaromatic group is preferred.

The indolizine compound represented by formula (I) can be synthesized by a known method. A most commonly used method is a synthesis method of performing the ring formation by reacting 2-alkylpyridine derivative and α-halogenoketone and treating the resulting quaternary ammonium salt in a basic aqueous solution. A general synthesis scheme (see, L. F. Tietze & Th. Eicher (translated by Seiichi Takano and Kunio Ogasawara), *Seimitsu Yuki Gosei-Jikken Manual, -Kaitei Dai 2-Han* (*Advanced Organic Synthesis, Manual for Experiments*, 2nd Ed.), pp. 344–345, Nankodo (1995)) is shown below and after that, specific examples of the compound of the present invention are set forth. Of course, the present invention is by no means limited thereto.

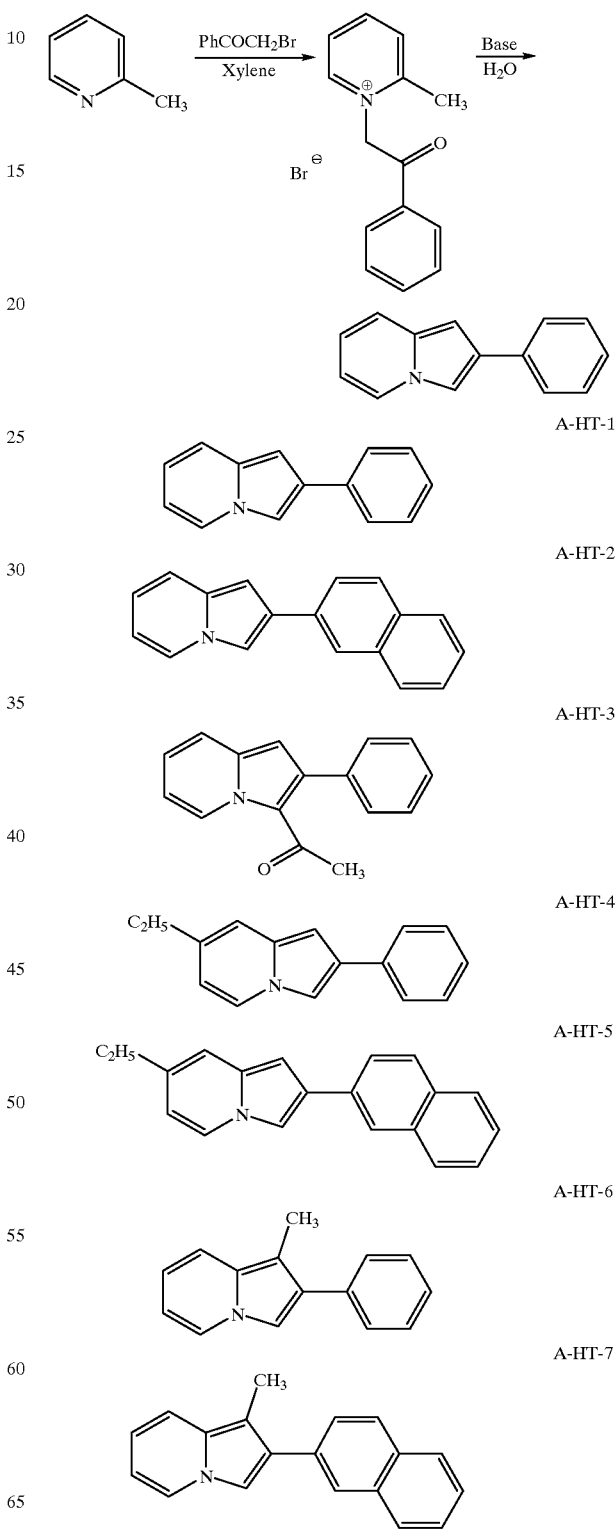

-continued
A-HT-8
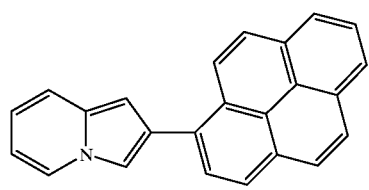
A-HT-9
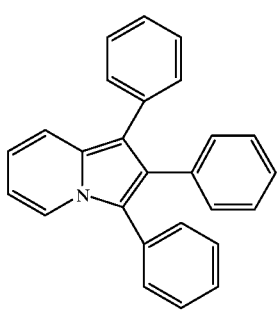
A-HT-10
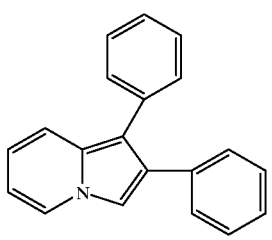
A-HT-11
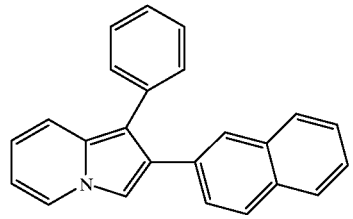
A-HT-12
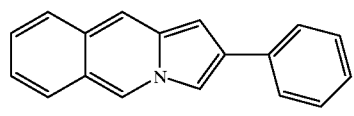
A-HT-13
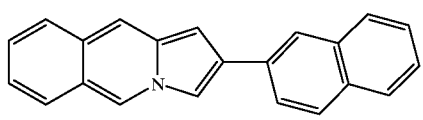
A-HT-14
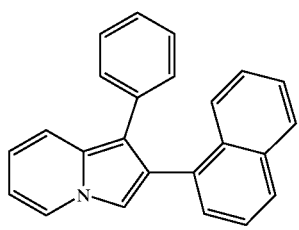
-continued
A-HT-15
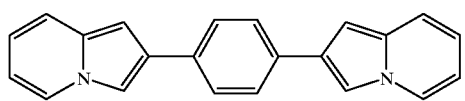
A-HT-16
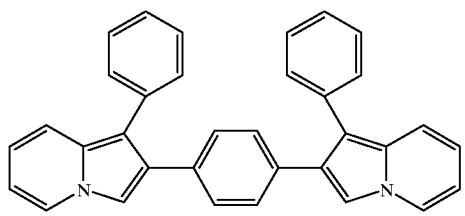
A-HT-17
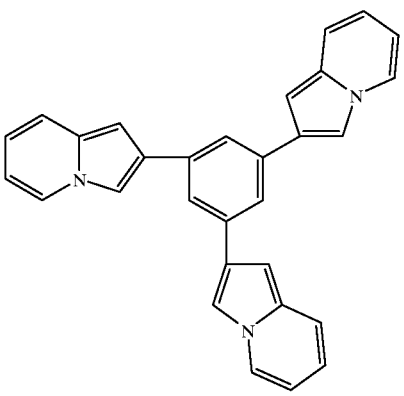
A-HT-18
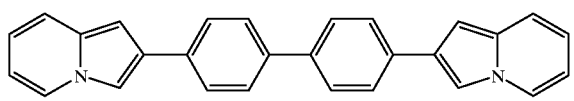
A-HT-19
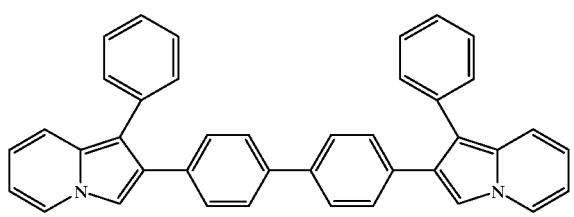
A-HT-20
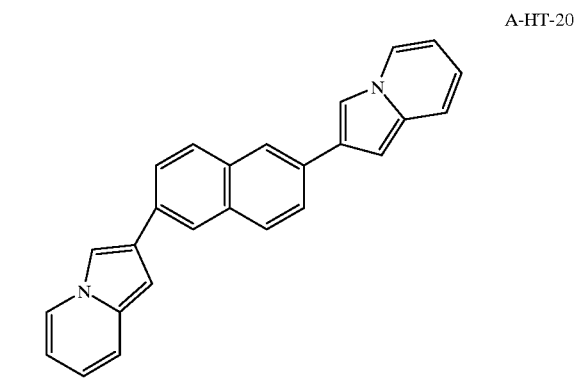

A-HT-21
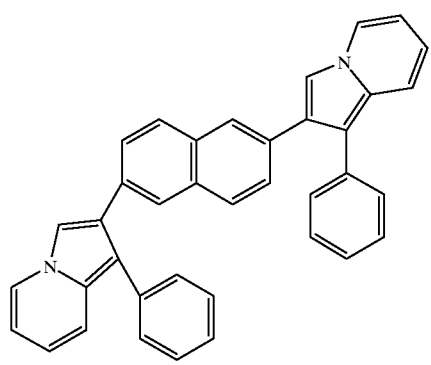
A-HT-22
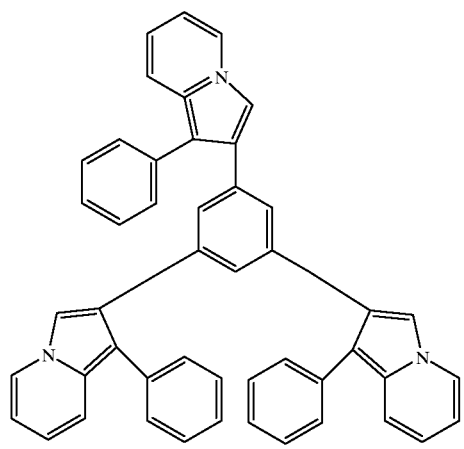
A-HT-23
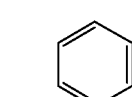
A-HT-24
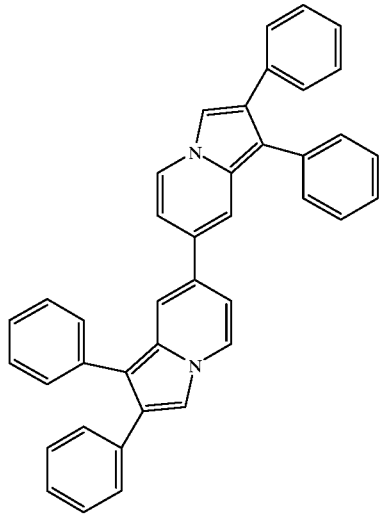
A-HT-25
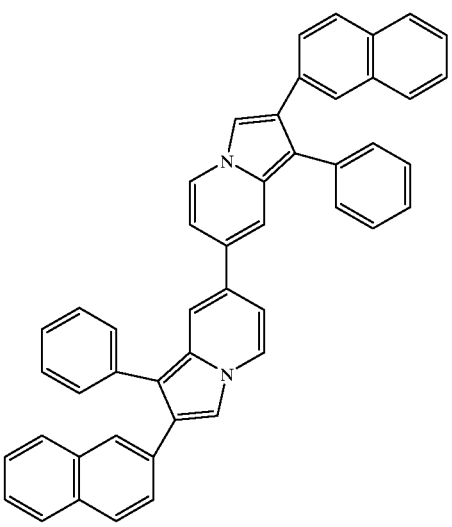
A-HT-26
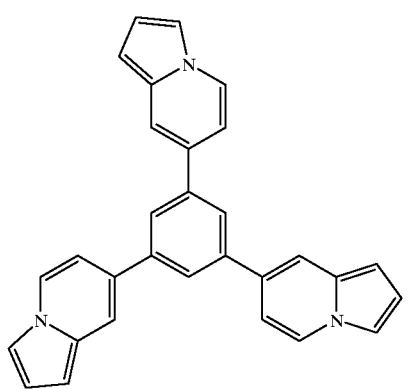

A-HT-27
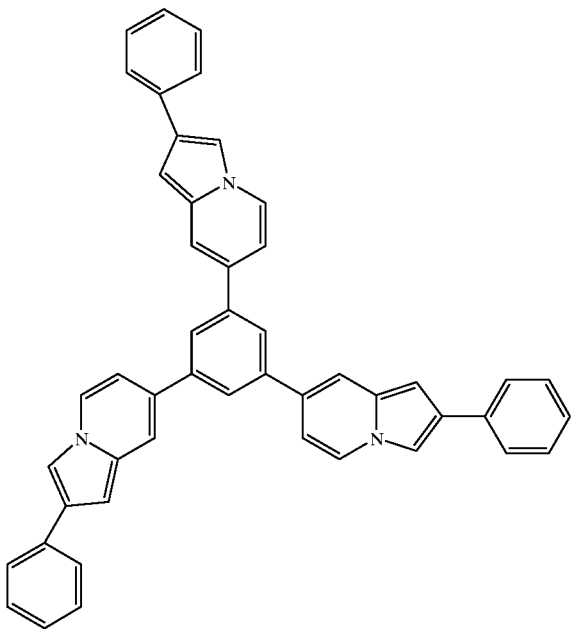
A-HT-28
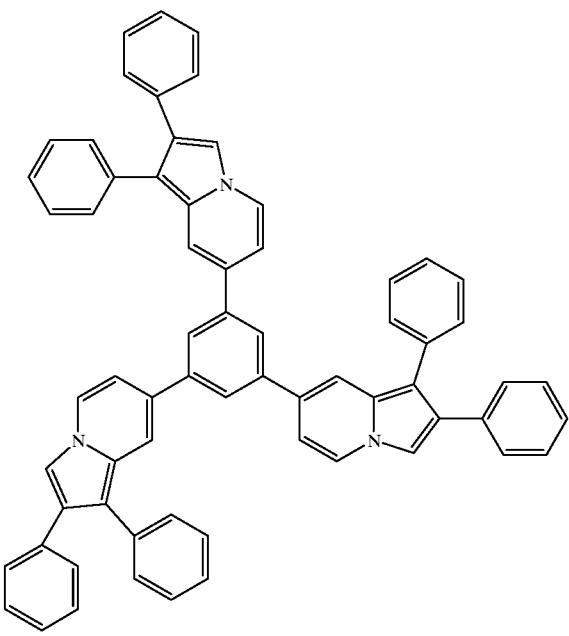
A-HT-29
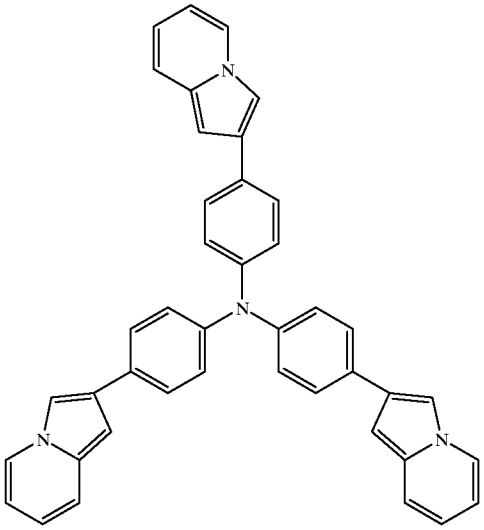
A-HT-30
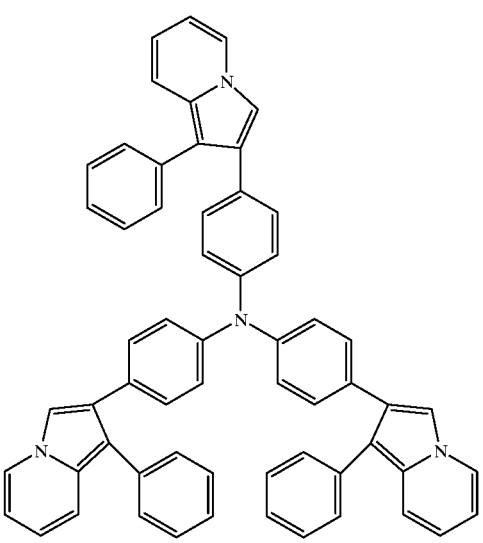
A-HT-31
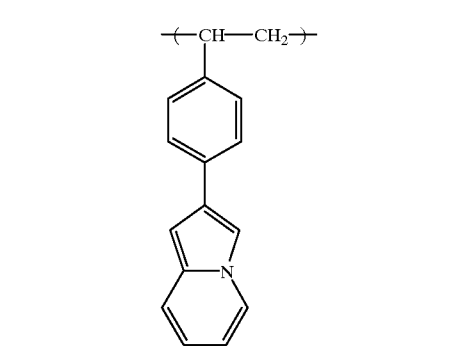

A-HT-32

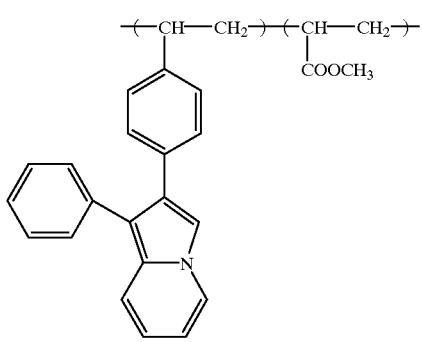

A-HT-33

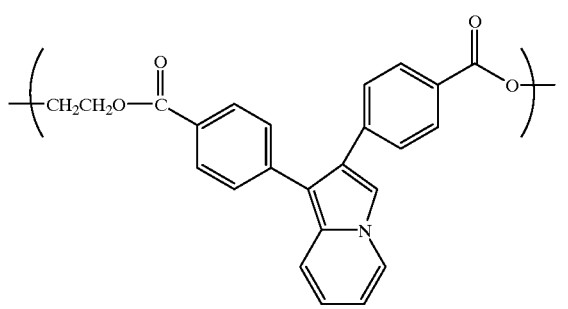

A-HT-34

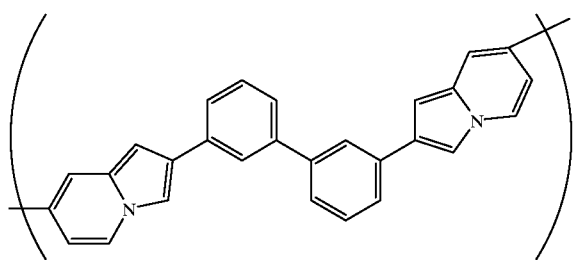

The compounds represented by formulae (II) and (III) are described below (II)

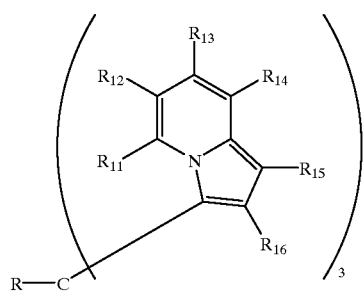

(III)

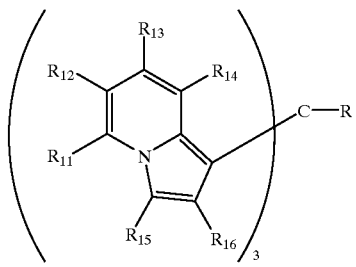

wherein $R_{11}$ to $R_{16}$ each independently represents a substituent selected from the group consisting of hydrogen atom, a substituted or unsubstituted alkyl group, a substituted or unsubstituted alkenyl group, a substituted or unsubstituted alkenyl group, a substituted or unsubstituted alkynyl group, a substituted or unsubstituted aryl group, a substituted or unsubstituted heterocyclic group, a substituted or unsubstituted alkoxy group, a substituted or unsubstituted aryloxy group, a substituted or unsubstituted alkylthio group, a substituted or unsubstituted arylthio group, a substituted or unsubstituted alkylamino group, a substituted or unsubstituted arylamino group, a substituted or unsubstituted alkylcarbonyl group, a substituted or unsubstituted arylcarbonyl group, a substituted or unsubstituted alkylsulfonyl group, a substituted or unsubstituted arylsulfonyl group, a substituted or unsubstituted alkoxycarbonyl group, a substituted or unsubstituted aryloxycarbonyl group, a substituted or unsubstituted carbamoyl group, a substituted or unsubstituted alkylcarbamoyl group, a substituted or unsubstituted arylcarbamoyl group, a substituted or unsubstituted sulfamoyl group, a substituted or unsubstituted alkylsulfamoyl group, a substituted or unsubstituted arylsulfamoyl group, a substituted or unsubstituted alkylcarbonyloxy group, a substituted or unsubstituted arylcarbonyloxy group, a substituted or unsubstituted alkylcarbonamido group, a substituted or unsubstituted arylcarbonamido group, a substituted or unsubstituted alkylsulfonamido group, a substituted or unsubstituted arylsulfonamido group, a substituted or unsubstituted urethane group, a substituted or unsubstituted ureido group and a substituted or unsubstituted carbonic acid ester group, the substituents selected from $R_{11}$ to $R_{16}$ may combine with each other to form a cyclic structure, and R represents hydrogen atom, an alkyl group, an aryl group or a heterocyclic group.

The compounds represented by formulae (II) and (III) are a trisheteroarylmethane where three indolizine rings are bonded to a methine group in the moiety at the 1- or 3-position.

$R_{11}$ to $R_{16}$, which are substituents common in formulae (II) and (III), each independently represents hydrogen atom, a substituted or unsubstituted alkyl group (preferably having from 1 to 20 carbon atoms, e.g., methyl, ethyl, n-propyl, i-propyl, n-butyl, t-butyl, octyl, dodecyl, benzyl, cyclopropyl, cyclohexyl), a substituted or unsubstituted alkenyl group (preferably having from 2 to 20 carbon atoms, e.g., ethynyl, propenyl, butenyl), a substituted or unsubstituted alkynyl group (preferably having from 2 to 20 carbon atoms, e.g., ethynyl, propynyl, butynyl), a substituted or unsubstituted aryl group (preferably having from 6 to 20 carbon atoms, e.g., phenyl, 1-naphthyl, 2-naphthyl, 4-methoxyphenyl, 3-methylphenyl, 9-phenanthryl, 9-anthryl, 1-pyrenyl), a substituted or unsubstituted heterocyclic group (preferably having from 1 to 20 carbon atoms; preferred examples of the heterocyclic ring include a 5-membered aromatic ring such as pyrrole, thiophene, furan, imidazole, pyrazole, thiazole, oxazole, triazole, oxadiazole and thiadiazole, a condensed ring thereof, a 6-membered ring such as pyridine, pyridazine, pyrimidine, pyrazine and triazine, and a condensed ring thereof; the heterocyclic ring may also be a non-aromatic heterocyclic ring represented by piperidine, tetrahydrofuran and tetrahydrothiophene), a substituted or unsubstituted alkylamino group (e.g., methylamino, dimethylamino, diethylamino, morpholino, pyrrolidino, piperidino, the alkylamino group is preferably a tertiary amino group having from 1 to 30 carbon atoms, more preferably from 1 to 16 carbon atoms), a substituted or unsubstituted arylamino group (including a heteroarylamino group; e.g., anilino, diphenylamino, 1-naphthylphenylamino, 2-naphthylphenylamino, N-ethylphenylamino; the arylamino group is preferably a tertiary amino group having from 6 to 30 carbon atoms, more preferably from 6 to 16 carbon atoms), a substituted or unsubstituted alkoxy group (preferably having from 1 to 30 carbon atoms, more preferably from 1 to 15 carbon atoms, e.g., methoxy, ethoxy, cyclohexyloxy), a substituted or unsubstituted aryloxy group (including a heteroaryloxy group; preferably having from 6 to 30 carbon atoms, more preferably from 6 to 15 carbon atoms, e.g., phenoxy, 1-naphthoxy, 4-phenylphenoxy), a substituted or unsubstituted alkylthio group (preferably having from 1 to 30 carbon atoms, more preferably from 1 to 15 carbon atoms, e.g., methylthio, ethylthio, cyclohexylthio), a substituted or unsubstituted arylthio group (including a heteroarylthio group; preferably having 6 to 30 carbon atoms, more preferably from 6 to 15 carbon atoms, e.g., phenylthio, tolylthio), a substituted or unsubstituted alkylcarbonyl group (preferably having from 1 to 30 carbon atoms, more preferably from 1 to 15 carbon atoms, e.g., acetyl, propionyl, butyroyl, lauroyl), a substituted or unsubstituted arylcarbonyl group (including a heteroarylcarbonyl group; preferably having from 6 to 30 carbon atoms, more preferably from 6 to 15 carbon atoms, e.g., benzoyl, naphthoyl), a substituted or unsubstituted alkylsulfonyl group (preferably having from 1 to 30 carbon atoms, more preferably from 1 to 15 carbon atoms, e.g., methanesulfonyl, ethanesulfonyl), a substituted or unsubstituted arylsulfonyl group (including a heteroarylsulfonyl group; preferably having from 6 to 30 carbon atoms, more preferably from 6 to 15 carbon atoms, e.g., benzenesulfonyl, p-toluenesulfonyl, 1-naphthalenesulfonyl), a substituted or unsubstituted alkoxycarbonyl group (preferably having from 1 to 30 carbon atoms, more preferably from 1 to 15 carbon atoms, e.g., methoxycarbonyl, ethoxycarbonyl, butoxycarbonyl), a substituted or unsubstituted aryloxycarbonyl group (including a heteroaryloxycarbonyl group; preferably having from 6 to 30 carbon atoms, more preferably from 6 to 15 carbon atoms, e.g., phenoxycarbonyl, 1-naphthoxycarbonyl), a substituted or unsubstituted alkylcarbonamido group (preferably having from 1 to 30 carbon atoms, more preferably from 1 to 15 carbon atoms, e.g., acetamido, propionylamido, butyroylamido), a substituted or unsubstituted arylcarbonamido group (including a heteroarylcarbonamido group; preferably having from 6 to 30 carbon atoms, more preferably from 6 to 15 carbon atoms, e.g., benzoylamido, N-methylbenzoylamido) a substituted or unsubstituted alkylsulfonamido group (preferably having from 1 to 30, more preferably from 1 to 15 carbon atoms, e.g., methanesulfonamido, ethanesulfonamido, butanesulfonamido), a substituted or unsubstituted arylsulfonamido group (including a heteroarylsulfonamido group; preferably having from 6 to 30 carbon atoms, more preferably from 6 to 15 carbon atoms, e.g., benzenesulfonamido, p-toluenesulfonamido, 1-naphthalenesulfonamido), a substituted or unsubstituted carbamoyl group, a substituted or unsubstituted alkylcarbamoyl group (preferably having from 1 to 30 carbon atoms, more preferably from 1 to 15 carbon atoms, e.g., methylcarbamoyl, dimethylcarbamoyl, diethylcarbamoyl, dioctylcarbamoyl), a substituted or unsubstituted arylcarbamoyl group (including a heteroarylcarbamoyl group; preferably having from 6 to 30 carbon atoms, more preferably from 6 to 15 carbon atoms, e.g., phenylcarbamoyl, diphenylcarbamoyl, methylphenylcarbamoyl), a substituted or unsubstituted sulfamoyl group, a substituted or unsubstituted alkylsulfamoyl group (preferably having from 1 to 30 carbon atoms, more preferably from 1 to 15 carbon atoms, e.g., methylsulfamoyl, dimethylsulfamoyl, diethylsulfamoyl, dioctylsulfamoyl), a substituted or unsubstituted arylsulfamoyl group (including a heteroarylsulfamoyl group; preferably having from 6 to 30 carbon atoms, more preferably from 6 to 15 carbon atoms, e.g., phenylsulfamoyl, diphenylsulfamoyl, methylphenylsulfamoyl), a substituted or unsubstituted alkylcarbonyloxy group (preferably having from 1 to 30 carbon atoms, more preferably from 1 to 15 carbon atoms, e.g., acetoxy, propionyloxy, butyroyloxy), a substituted or unsubstituted arylcarbonyloxy group (including a heteroarylcarbonyloxy group; preferably having from 6 to 30 carbon atoms, more preferably from 6 to 15 carbon atoms, e.g., benzoyloxy, 1-naphthoyloxy), a substituted or unsubstituted urethane group (preferably having from 1 to 30 carbon atoms, more preferably from 1 to 15 carbon atoms, e.g., methoxycarbonamido, phenoxycarbonamido, methylaminocarbonamido), a substituted or unsubstituted ureido group (preferably having from 1 to 30 carbon atoms, more preferably from 1 to 15 carbon atoms, e.g., methylaminocarbonamido, dimethylaminocarbonamido, diphenylaminocarbonamido) or a substituted or unsubstituted carbonic acid ester group (preferably having from 1 to 30 carbon atoms, more preferably from 1 to 15 carbon atoms, e.g., methoxycarbonyloxy, phenoxycarbonyloxy).

R represents hydrogen atom, an alkyl group (preferably having from 1 to 20 carbon atoms, e.g., methyl, ethyl, n-propyl, i-propyl, n-butyl, t-butyl, octyl, dodecyl, benzyl, cyclopropyl, cyclohexyl), an aryl group (preferably having from 6 to 20 carbon atoms, e.g., phenyl, 1-naphthyl, 2-naphthyl, 4-methoxyphenyl, 3-methylphenyl, 9-phenanthryl, 9-anthryl, 1-pyrenyl) or a heterocyclic group (preferably having from 1 to 20 carbon atoms; preferred examples of the heterocyclic ring include a 5-membered aromatic ring such as pyrrole, thiophene, furan, imidazole, pyrazole, thiazole, oxazole, triazole, oxadiazole and thiazole, a condensed ring thereof, a 6-membered aromatic ring such as pyridine, pyridazine, pyrimidine, pyrazine and triazine, and a condensed ring thereof; the heterocyclic ring may also be a non-aromatic heterocyclic ring represented by piperidine, tetrahydrofuran and tetrahydrothiophene). R is preferably hydrogen atom.

Out of $R_{11}$ to $R_{16}$, at least one of $R_{11}$ to $R_{14}$ is preferably substituted by a substituent except for hydrogen atom, or at least one of $R_{15}$ and $R_{16}$ is preferably substituted by a substituent except for hydrogen atom, and the substituent is preferably selected from the group consisting of an alkyl group, an aryl group, an alkenyl group, an alkynyl group and a heterocyclic group. The compound is more preferably a compound where at least one of $R_{15}$ and $R_{16}$ has two or more benzene rings or at least one substituent selected from a condensed polycycloaromatic hydrocarbon group and a heteroaromacyclic group.

The compounds represented by formulae (II) and (III) each may be a compound which itself finally works out to a structure capable of exerting the function. Alternatively, the final structure may be derived from a precursor of the compound by using it in an organic EL device and after or during the fabrication of the device, physically or chemically after-treating the device. The compounds represented by formulae (II) and (III) each preferably has a molecular weight of 200 to 5,000, more preferably from 300 to 2,000.

The compounds represented by formulae (II) and (III) can be synthesized by a known method. The indolizine compound can be synthesized by the Chichibabin method (a ring formation reaction through production of a pyridinium salt from a picoline derivative and an α-halocarbonyl compound and subsequent treatment with a basic aqueous solution). The compounds represented by formulae (II) and (III) each can be derived from this indolizine compound by treating the compound in anhydrous methanol in the presence of a sulfuric acid catalyst using an ortho-ester such as ethyl orthoformate (a method described in *Chem. Ber.*, 120, 239–242 (1987)). A general synthesis scheme is disclosed below and after that, specific examples of the compounds of the present invention are set forth. The present invention is not limited to those specific examples.

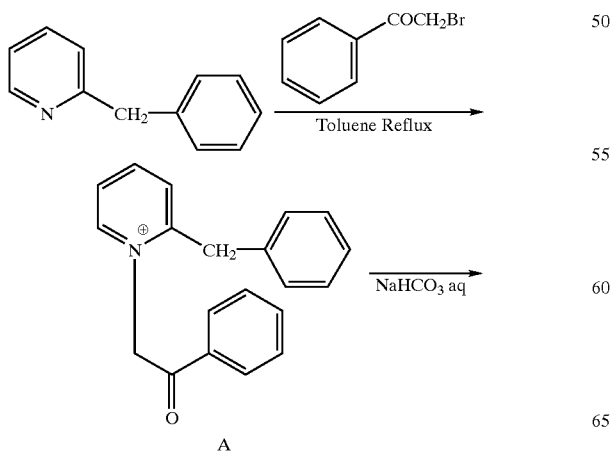

A

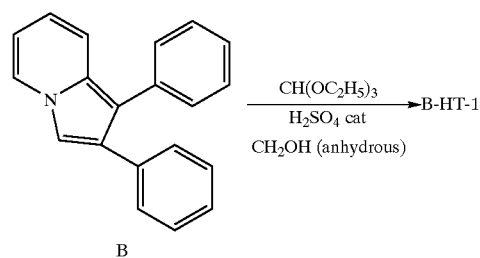

B

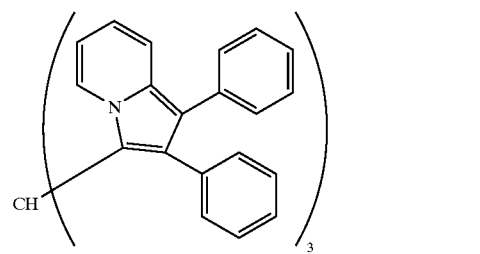

B-HT-1

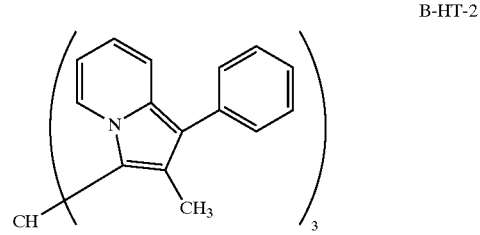

B-HT-2

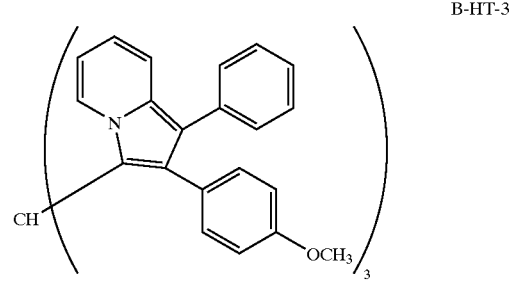

B-HT-3

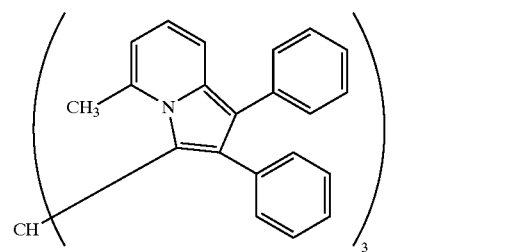

B-HT-4

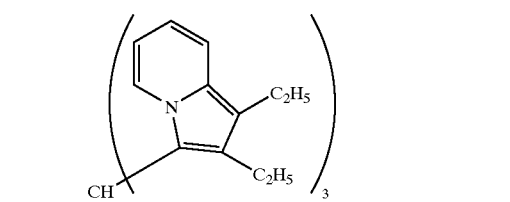

B-HT-5

B-HT-6
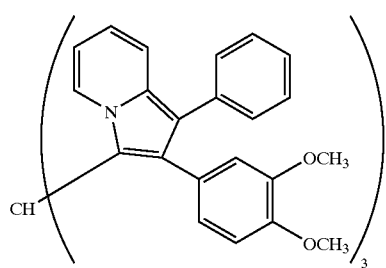
B-HT-12
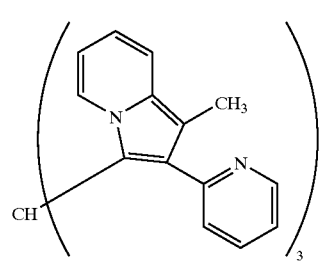
B-HT-7
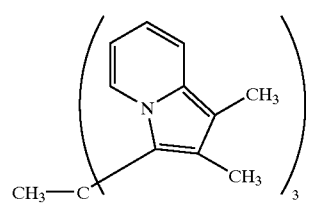
B-HT-13
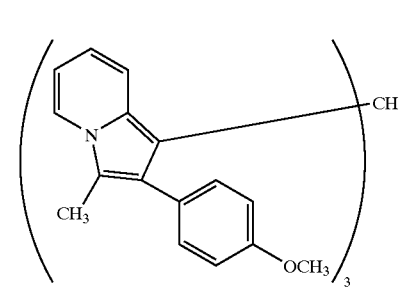
B-HT-8
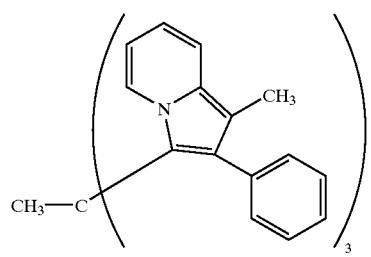
B-HT-14
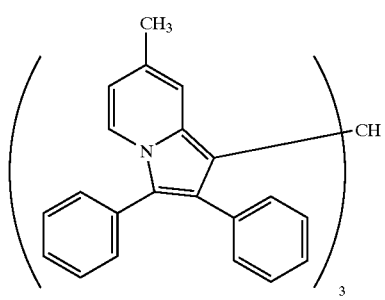
B-HT-9
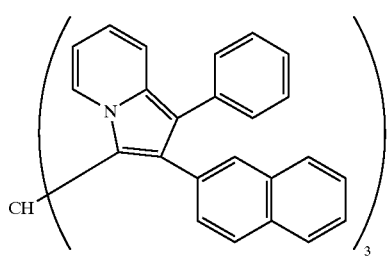
B-HT-15
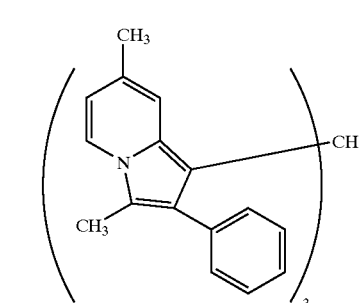
B-HT-10
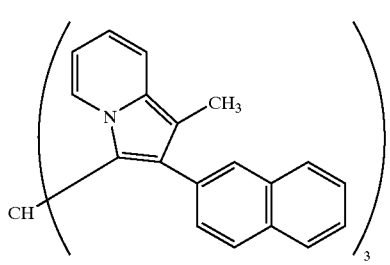
B-HT-11
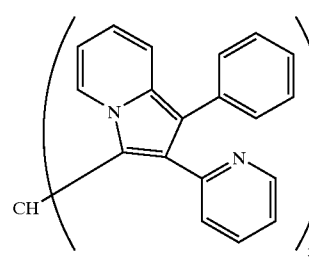
B-HT-16
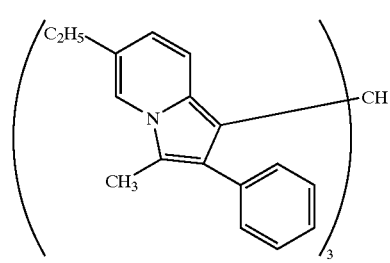

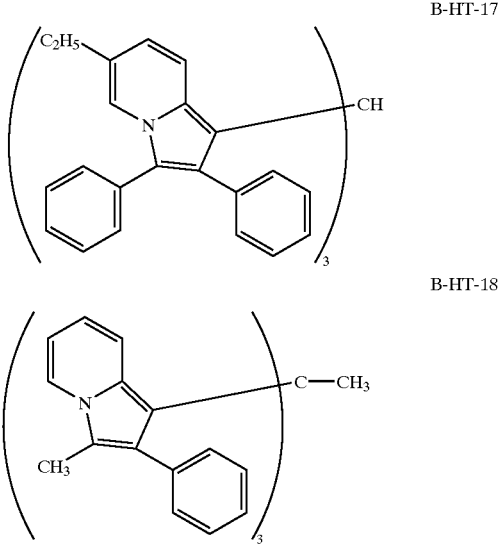

B-HT-17

B-HT-18

[Synthesis of Compound B-HT-1]

(Synthesis of Compound A)

To 1,200 ml of toluene, 169.2 g (1.0 mol) of 2-benzylpyridine was added while stirring to form a uniform solution. The temperature of this solution was elevated to 80° C. and thereto, 199 g (1.0 mol) of phenacyl bromide was gradually added while stirring. The stirring was continued, as a result, crystals were precipitated. The temperature was elevated to the reflux conditions and the reaction was continued for another 1 hour while stirring. After cooling, the precipitated crystals were separated by filtration and then washed with toluene and subsequently with n-hexane to obtain 327 g of crystals of Compound A.

(Synthesis of Compound B)

Into 3,000 ml-volume three-neck flask, 295 g (0.8 mol) of Compound A was charged and after adding 1,000 ml of water, the compound was dissolved while stirring. A nitrogen stream was passed therethrough, 84 g (1.0 mol) sodium hydrogencarbonate was added thereto, and the inner temperature was elevated up to 85° C. in a steam bath while stirring. The stirring was continued, as a result, vigorous bubbling took place and pale yellow crystals were precipitated. The reaction was continued for another 1 hour and after cooling to room temperature, the precipitated crystals were separated by filtration. These crystals were recrystallized from a acetonitrile-water mixed solvent to obtain 186 g of crystals of Compound B.

(Synthesis of Compound B-HT-1)

To 300 ml of dehydrated methanol for organic synthesis, 67.3 g (0.25 mol) of Compound B was added and stirred. Thereto, 11.8 g (0.08 mol) of ethyl orthoformate and 1 ml of concentrated sulfuric acid were added and reacted under reflux for 2 hours. At first, the color of the solution was turned to deep blue green and after a while, white crystals were precipitated. After the completion of reaction, the crystals still in the hot state were filtered and the obtained crystals were recrystallized from a tetrahydrofuran-methanol mixed solvent to obtain 48 g of crystals of Compound B-HT-1.

The compound represented by formula (IV) is described below. The compound represented by formula (IV) is a compound which can be generically called an indolizine boronic acid derivative. The compound of the present invention is characterized in that the substitution site thereof is the 5-position of the indolizine ring. In formula (IV), the substituents $R_{21}$ to $R_{26}$ each represents a substituent selected from the group consisting of hydrogen atom, a substituted or unsubstituted alkyl group, a substituted or unsubstituted alkenyl group, a substituted or unsubstituted alkynyl group, a substituted or unsubstituted aryl group, a substituted or unsubstituted heterocyclic group, a substituted or unsubstituted alkoxy group, a substituted or unsubstituted aryloxy group, a substituted or unsubstituted heteroaryloxy group, substituted or unsubstituted alkylthio group, a substituted or unsubstituted arylthio group, a substituted or unsubstituted heteroarylthio group, a substituted or unsubstituted alkylamino group, a substituted or unsubstituted arylamino group, a substituted or unsubstituted heteroarylamino group, a substituted or unsubstituted alkylcarbonyl group, a substituted or unsubstituted arylcarbonyl group, a substituted or unsubstituted heteroarylcarbonyl group, a substituted or unsubstituted alkylsulfonyl group, a substituted or unsubstituted arylsulfonyl group, a substituted or unsubstituted heteroarylsulfonyl group, a substituted or unsubstituted alkoxycarbonyl group, a substituted or unsubstituted aryloxycarbonyl group, a substituted or unsubstituted heteroaryloxycarbonyl group, a substituted or unsubstituted alkylcarbamoyl group, a substituted or unsubstituted arylcarbamoyl group, a substituted or unsubstituted heteroarylcarbamoyl group, a substituted or unsubstituted alkylsulfamoyl group, a substituted or unsubstituted arylsulfamoyl group, a substituted or unsubstituted heteroarylsulfamoyl group, a substituted or unsubstituted alkylcarbonyloxy group, a substituted or unsubstituted arylcarbonyloxy group, a substituted or unsubstituted heteroarylcarbonyloxy group, a substituted or unsubstituted alkylcarbonamido group, a substituted or unsubstituted arylcarbonamido group, a substituted or unsubstituted heteroarylcarbonamido group, a substituted or unsubstituted alkylsulfonamido group, a substituted or unsubstituted arylsulfonamido group, a substituted or unsubstituted heteroarylsulfonamido group, a substituted or unsubstituted urethane group, a substituted or unsubstituted ureido group and a substituted or unsubstituted carbonic acid ester group. In the present invention, the compound represented by formula (IV) is obtained through a metalation reaction, therefore, the substituents $R_{21}$ to $R_{26}$ are preferably not substituted by hydrogen atom which may be metalated. For example, in all substituents, a dissociative proton (e.g., —OH, —NH, —SH) substituted to a hetero atom is preferably not present. In the case of an alkyl group, the carbon atom bonded to the indolizine ring is preferably not substituted by hydrogen atom. The alkenyl group, aryl group or heteroaryl group is preferably not substituted by a halogen atom such as bromo group or iodo group. Examples of the substituent except for hydrogen atom, which can be preferably substituted to $R_{21}$ to $R_{26}$, include a t-butyl group, a phenyl group and a naphthyl group. The substituents selected from $R_{21}$ to $R_{26}$ can combine with each other to form a cyclic structure.

$R_{27}$ and $R_{28}$ each represents hydrogen atom, an alkyl group, an aryl group or a heterocyclic group, preferably hydrogen atom or an alkyl group. $R_{27}$ and $R_{28}$ may combine with each other to form a cyclic structure.

In the present invention, the compound represented by formula (IV) is synthesized by a method of metalating an indolizine compound and then reacting the metalated compound with a boric acid ester compound. The term "metalation" as used herein means a reaction where an indolizine compound is treated in an ether-base solvent under low-temperature conditions using an alkali metal compound, an alkaline earth metal compound, metal zinc or an alkyl- or aryl-substitution product thereof to displace the hydrogen atom at the 5-position of the indolizine ring by a metal atom. Among alkali metal compounds, alkaline earth metal compounds and the like, preferred are lithium, sodium, potassium, calcium, magnesium and zinc, more preferred are lithium and magnesium. In the metalation reaction, a metal may be used as it is but in the case of lithium and the like, an exchange reaction with a commercially available alkyl-substitution product is preferably used in view of safety and operability. The boronic acid ester is preferably a trialkoxyborane derivative.

The metalation reaction and the reaction between the metalated indolizine compound and a boronic ester compound each is preferably performed at 20° C. or less, more preferably 0° C. or less, still more preferably −20° C. or less. The reaction time is preferably from 5 minutes to 10 hours, more preferably from 10 minutes to 5 hours, still more preferably from 30 minutes to 2 hours. The compound used in the metalation reaction and the boric acid ester compound each is preferably used in an amount of 0.1 to 100 molar equivalent, more preferably from 0.5 to 10 molar equivalent, still more preferably from 1 to 5 molar equivalent, to the indolizine compound as an objective of the reaction.

The compound (V) is described below. The compound represented by formula (V) is a compound in which an alkenyl group, an aryl group or a heteroaryl group is substituted at the 5-position of the indolizine ring. This compound is synthesized by the reaction of the compound represented by formula (IV) with a vinyl halide, aryl halide or heteroaryl halide compound. This reaction can be performed by applying a Suzuki coupling reaction known in the field of organic synthesis chemistry (see, Katsuyuki Ogura, *Yuki Jinmei Han'no* (*Named Reactions in Organic Chemistry*), Asakura Shoten (1997)). In practice, the reaction is preferably performed using a palladium catalyst and a phosphine derivative as a phosphorus-base compound. In this reaction, the reaction temperature is preferably from 50 to 250° C., more preferably from 100 to 200° C. The vinyl halide or the like is preferably used in an amount of 0.5 to 5 molar equivalent to the compound represented by formula (IV).

$R_{20}$ represents an alkenyl group (preferably having from 2 to 20 carbon atoms, e.g., 2-phenylvinyl), an aryl group (preferably having from 6 to 20 carbon atoms, e.g., phenyl, 1-naphthyl, 2-naphthyl, 4-methoxyphenyl, 3-methylphenyl, 9-phenanthryl, 9-anthryl, 1-pyrenyl) or a heteroaryl group (preferably having from 1 to 20 carbon atoms; preferred examples of the heterocyclic ring include a 5-membered aromatic ring such as pyrrole, thiophene, furan, imidazole, pyrazole, thiazole, oxazole, triazole, oxadiazole and thiadiazole, a condensed ring thereof, a 6-membered aromatic ring such as pyridine, pyridazine, pyrimidine, pyrazine and triazine, and a condensed ring thereof).

In the present invention, the compound represented by formula (V) is used as the organic light-emitting device material. In the case of using the compound represented by formula (V) as the organic light-emitting device material, when a low molecular compound is used, the molecular weight thereof is preferably from 200 to 5,000, more preferably from 300 to 2,000. A polymer compound starting from the compound represented by formula (V) may also be used. In this case, the polymer may be used by introducing a polymerizable group such as an ethylenically unsaturated bond or a polymerizable group capable of bringing out polycondensation, such as carboxyl group, amino group and ester group, into $R_{21}$ to $R_{26}$ or $R_{20}$ and causing polymerization of the group. Also, the polymer may be formed while allowing a precursor of the compound represented by formula (V) to form the skeleton of the compound represented by formula (V). When a high molecular compound is used, the average molecular weight (Mw) is preferably from 2,000 to 1,000,000, more preferably from 5,000 to 100,000.

The basic skeleton of the indolizine compound included in formula (IV) can be synthesized by a known method. The indolizine compound can be synthesized by the Chichibabin method (a ring formation reaction through production of a pyridinium salt from a picoline derivative and an α-halocarbonyl compound and subsequent treatment with a basic aqueous solution). The compound represented by formula (IV) is synthesized by reacting the metalated indolizine compound with a boric acid ester. Through a Suzuki coupling reaction between this compound and a vinyl halide, aryl halide or heteroaryl halide compound, the compound of formula (V) can be synthesized.

A general synthesis scheme is disclosed below and after that, specific examples of the compounds of the present invention are set forth. Of course, the present invention is not limited to these specific examples.

Synthesis Route of Compound INB-1 of Formula (IV)

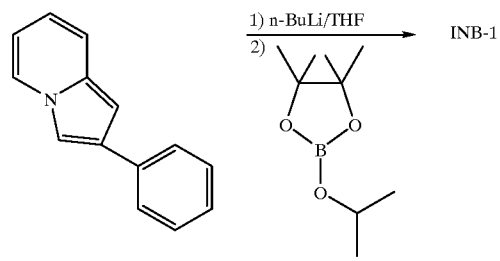

Synthesis Route of Compound C-HT-10 of Formula (V)

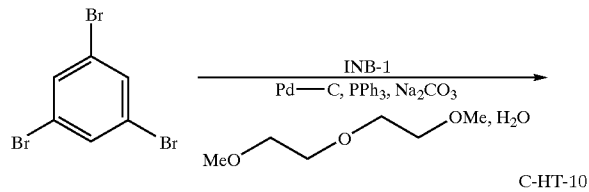

Examples of Compound Represented by Formula (IV)
INB-1
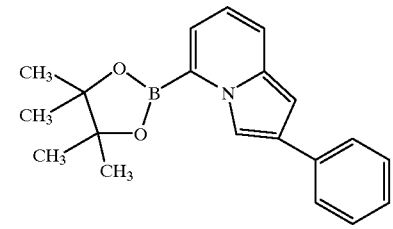
INB-2
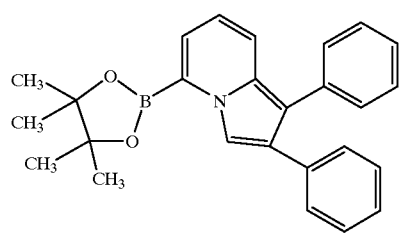
INB-3
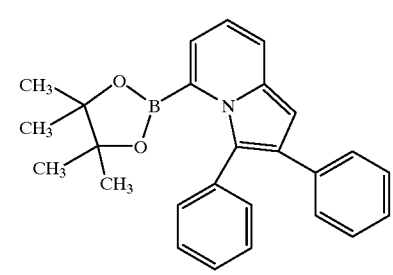
INB-4
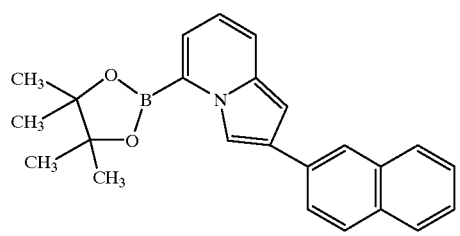
INB-5
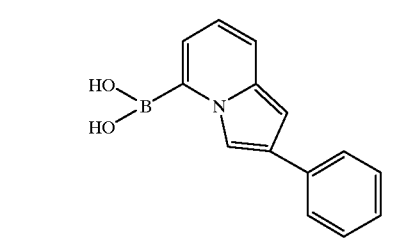
INB-6
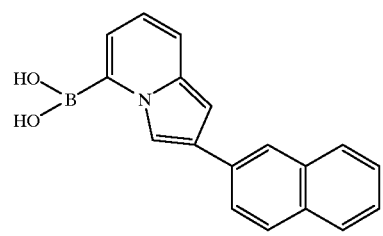
INB-7
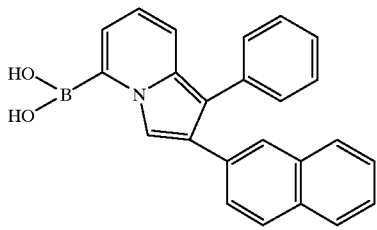
INB-8
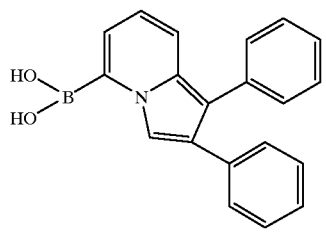
INB-9
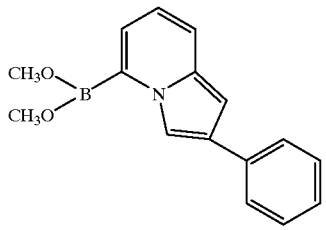
INB-10
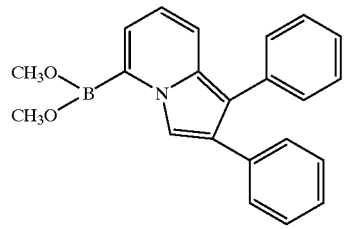
INB-11
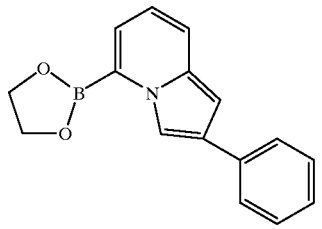
INB-12
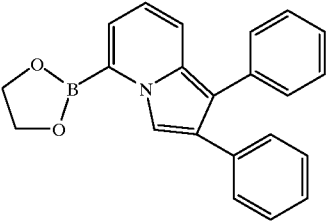

Examples of Compound Represented by Formula (V)
C-HT-1
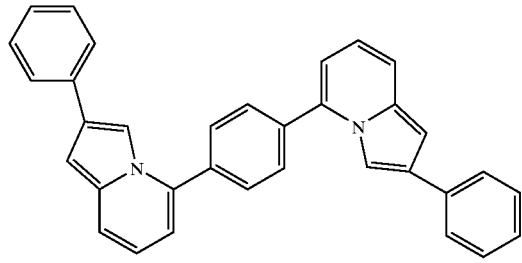
C-HT-2
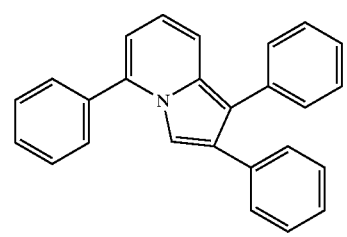
C-HT-3
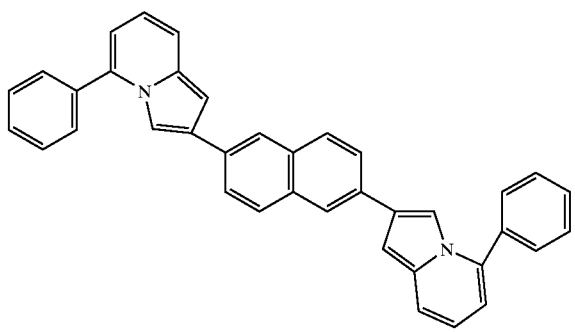
C-HT-4
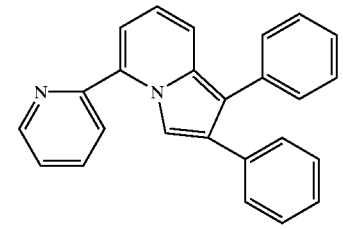
C-HT-5
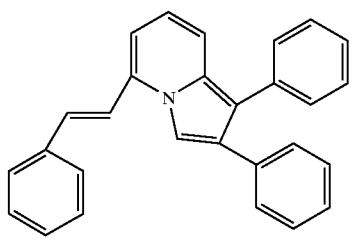
C-HT-6
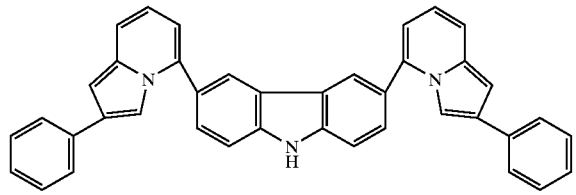
C-HT-7
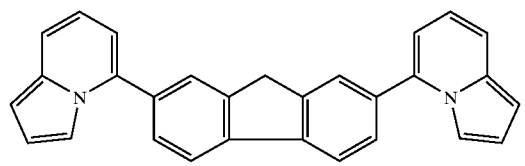
C-HT-8
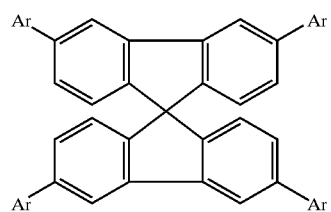
Ar =
C-HT-9
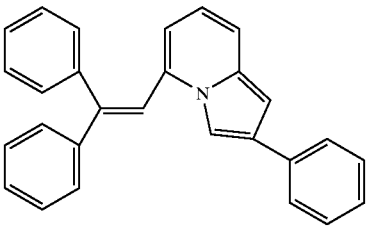
C-HT-10
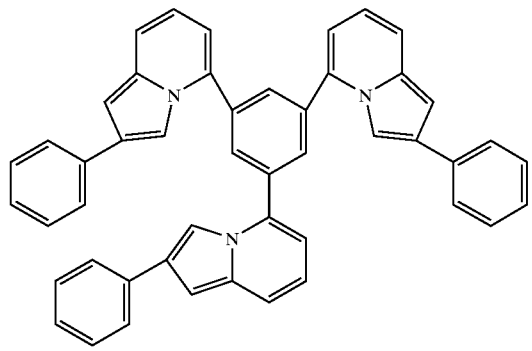

C-HT-11
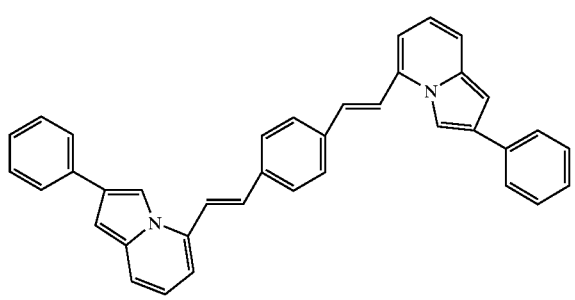

C-HT-16
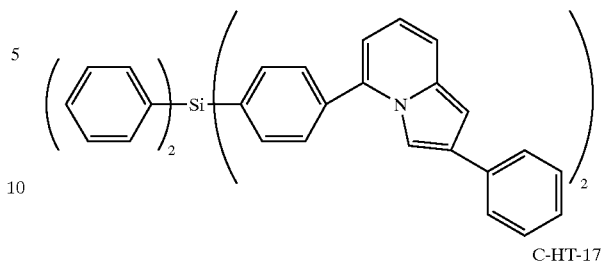

C-HT-17
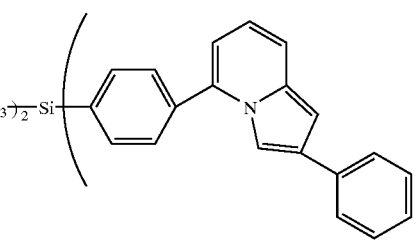

C-HT-12
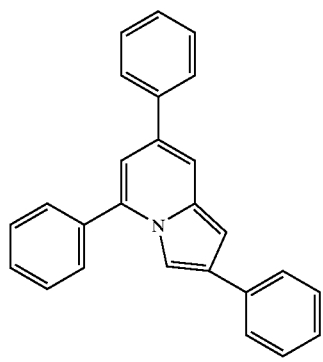

C-HT-18
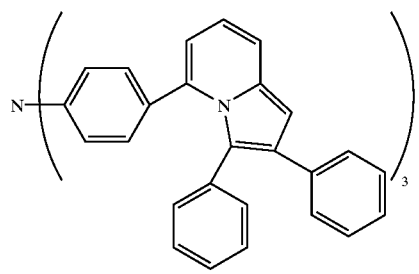

C-HT-13
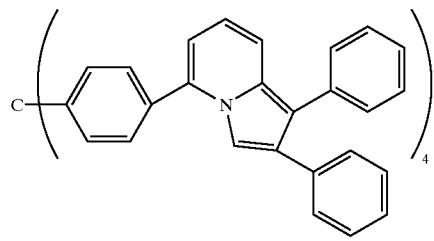

C-HT-19
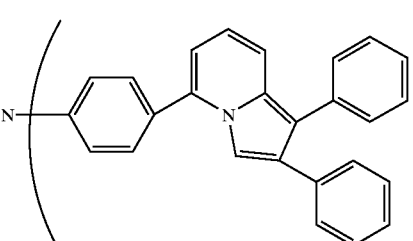

C-HT-14
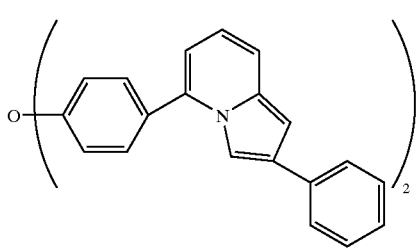

C-HT-20
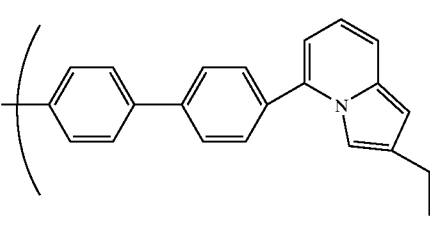

C-HT-15
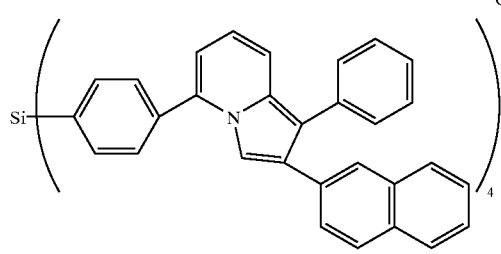

The light-emitting device containing the compound of the present invention is described below. The method for forming the organic layer of the light-emitting device containing the compound of the present invention is not particularly limited but a resistance heating evaporation, electron beam, sputtering, molecular lamination, coating, printing or inkjet method is used. In view of the properties and production, a resistance heating evaporation method and a coating method are preferred.

The light-emitting device of the present invention is a device fabricated by forming a light-emitting layer or a plurality of organic compound thin films containing a light-emitting layer between a pair of electrodes of anode and cathode. In addition to the light-emitting layer, a hole-injecting layer, a hole-transporting layer, an electron-injecting layer, an electron-transporting layer, a protective layer and the like may be provided. These layers each may have a function other than the function intended. For forming each layer, various materials may be used.

The anode feeds holes to the hole-injecting layer, the hole-transporting layer or the light-emitting layer, and a metal, an alloy, a metal oxide, an electrically conducting compound or a mixture thereof may be used therefor. A material having a work function of 4 eV or more is preferred. Specific examples thereof include electrically conducting metal oxides such as tin oxide, zinc oxide, indium oxide and indium tin oxide (ITO), metals such as gold, silver, chromium and nickel, a mixture or laminate of the metal with the electrically conducting metal oxide, inorganic electrically conducting materials such as copper iodide and copper sulfide, organic electrically conducting materials such as polyaniline, polythiophene and polypyrrole, and a laminate of the material with ITO. Among these, electrically conducting metal oxides are preferred and in view of productivity, high electrical conductivity and transparency, ITO is more preferred. The thickness of the anode may be freely selected depending on the material used, however, it is usually in the range of preferably from 10 nm to 5 $\mu$m, more preferably from 50 nm to 1 $\mu$m, still more preferably from 100 to 500 nm.

The anode is usually a layer formed on a soda lime glass, an alkali-free glass or a transparent resin substrate. In the case of using a glass, the constructive material therefor is preferably an alkali-free glass so as to reduce the ion dissolved out from the glass. In the case of using a soda lime glass, the glass is preferably subjected to barrier coating with silica or the like. The thickness of the substrate is not particularly limited as long as it is sufficiently large to maintain the mechanical strength, however, in the case of using a glass, the thickness is usually 0.2 mm or more, preferably 0.7 mm or more. The anode may be prepared by various methods according to the material used and for example, in the case of ITO, the layer is formed by an electron beam method, a sputtering method, a resistance heating evaporation method, a chemical reaction method (sol-gel process) or a method of coating an indium tin oxide dispersion. By subjecting the anode to rinsing or other treatments, the device driving voltage can be lowered or the light-emission efficiency can be increased. For example, in the case of ITO, a UV-ozone treatment and a plasma treatment are effective.

The cathode feeds electrons to the electron-injecting layer, the electron-transporting layer or the light-emitting layer and is selected by taking account of the adhesion to the layer adjacent to the negative electrode, such as an electron-injecting layer, an electron-transporting layer and a light-emitting layer, the ionization potential and the stability. As the material for the cathode, a metal, an alloy, a metal halide, a metal oxide, an electrically conducting compound or a mixture thereof may be used and specific examples thereof include an alkali metal (e.g., Li, Na, K, Cs) and fluoride and oxide thereof, an alkaline earth metal (e.g., Mg, Ca) and fluoride and oxide thereof, gold, silver, lead, aluminum, a sodium-potassium alloy or mixed metal, a lithium-aluminum alloy or mixed metal, a magnesium-silver alloy or mixed metal, and a rare earth metal such as indium and ytterbium. Among these, preferred are materials having a work function of 4 eV or less, more preferred are aluminum, a lithium-aluminum alloy or mixed metal, and a magnesium-silver alloy or mixed metal. The cathode may have not only a single layer structure of the above-described compound or a mixture of those compounds but also a laminate structure containing the above-described compound or a mixture of those compounds. The thickness of the cathode may be freely selected depending on the material used, however, it is usually in the range of preferably from 10 nm to 5 $\mu$m, more preferably from 50 nm to 1 $\mu$m, still more preferably from 100 nm to 1 $\mu$m. The cathode may be manufactured by an electron beam method, a sputtering method, a resistance heating evaporation method or a coating method, and a sole metal may be deposited or two or more components may be simultaneously deposited. Furthermore, a plurality of metals may be co-deposited to form an alloy electrode, or an alloy previously prepared may be deposited. The anode and the cathode each preferably has a low sheet resistance of hundreds of $\Omega/\square$ or less.

The material for the light-emitting layer may be any as long as it can form a layer having a function of injecting holes from the anode, hole-injecting layer or hole-transporting layer and at the same time injecting electrons from the cathode, electron-injecting layer or electron-transporting layer upon application of an electric field, a function of transferring charges injected, or a function of offering a chance to the hole and the electron to recombine and emit light. The light-emitting layer is preferably a layer containing an amine compound of the present invention but other light-emitting materials may also be used. Examples thereof include various metal complexes and orthometalated complexes including metal complexes and rare earth complexes of benzoxazole derivative, benzimidazole derivative, benzothiazole derivative, styrylbenzene derivative, polyphenyl derivative, diphenylbutadiene derivative, tetraphenylbutadiene derivative, naphthalimide derivative, coumarin derivative, perylene derivative, perynone derivative, oxadiazole derivative, aldazine derivative, pyralidine derivative, cyclopentadiene derivative, bisstyrylanthracene derivative, quinacridone derivative, pyrrolopyridine derivative, thiazolopyridine derivative, cyclopentadiene derivative, styrylamine derivative, aromatic dimethylidyne compound and 8-quinolinol derivative, and polymer compounds such as polythiophene, polyphenylene and polyphenylenevinylene. The thickness of the light-emitting layer is not particularly limited, however, it is usually in the range of preferably from 1 nm to 5 $\mu$m, more preferably from 5 nm to 1 $\mu$m, still more preferably from 10 to 500 nm.

The method for forming the light-emitting layer is not particularly limited and a resistance heating evaporation method, an electron beam method, a sputtering method, a molecular lamination method, a coating method (e.g., spin coating, casting, dip coating), an LB method, a printing method or an inkjet method may be used. Among these, preferred are a resistance heating evaporation method and a coating method.

The material for the hole-injecting layer and the hole-transporting layer may be any as long as it has any one of a function of injecting holes from the anode, a function of transporting holes and a function of blocking electrons injected from the cathode. Specific examples thereof include electrically conducting high molecular oligomers such as carbazole derivative, triazole derivative, oxazole derivative, oxadiazole derivative, imidazole derivative, polyarylalkane derivative, pyrazoline derivative, pyrazolone derivative, phenylenediamine derivative, arylamine derivative, amino-substituted chalcone derivative, styrylanthracene derivative, fluorenone derivative, hydrazone derivative, stilbene derivative, silazane derivative, aromatic tertiary amine compound, styrylamine compound, aromatic dimethylidyne-base compound, porphyrin-base compound, polysilane-base compound, poly(N-vinylcarbazole) derivative, aniline-base copolymer, thiophene oligomer and polythiophene. In the present invention, the compound represented by formula (I), (II), (III), (IV) or (V) is used to this purpose. The hole-injecting layer and the hole-transporting are not particularly limited on the thickness, however, the thickness is usually in the range of preferably from 1 nm to 5 µm, more preferably from 5 nm to 1 µm, still more preferably from 10 to 500 nm. The hole-injecting layer and the hole-transporting layer each may have a single layer structure comprising one or more of the above-described materials or may have a multi-layer structure comprising a plurality of layers which are the same or different in the composition.

The hole-injecting layer and the hole-transporting layer each is formed by a vacuum evaporation method, an LB method, an inkjet method, a method of dissolving or dispersing the above-described hole-injecting and transporting agent in a solvent and coating the solution or dispersion (e.g., spin coating, casting, dip coating) or a printing method. In the case of the coating method, the material can be dissolved or dispersed together with a resin component. Examples of the resin component include polyvinyl chloride, polycarbonate, polystyrene, polymethyl methacrylate, polybutyl methacrylate, polyester, polysulfone, polyphenylene oxide, polybutadiene, poly(N-vinylcarbazole), hydrocarbon resin, ketone resin, phenoxy resin, polyamide, ethyl cellulose, vinyl acetate, ABS resin, polyurethane, melamine resin, unsaturated polyester resin, alkyd resin, epoxy resin and silicone resin.

The material for the electron-injecting layer and electron-transporting layer may be any as long as it has any one of a function of injecting electrons from the cathode, a function of transporting electrons and a function of blocking holes injected from the anode. Specific examples thereof include various metal complexes including metal complexes of triazole derivative, oxazole derivative, oxadiazole derivative, fluorenone derivative, anthraquinodimethane derivative, anthrone derivative, diphenylquinone derivative, thiopyran dioxide derivative, carbodiimide derivative, fluorenylidenemethane derivative, distyrylpyrazine derivative, heterocyclic tetracarboxylic acid anhydrides (e.g., naphthalene perylene), phthalocyanine derivative and 8-quinolinol derivative, and metal complex containing metal phthalocyanine, benzoxazole or benzothiazole as a ligand. The electron-injecting layer and the electron-transporting layer are not particularly limited on the thickness, however, the thickness is usually in the range of preferably from 1 nm to 5 µm, more preferably from 5 nm to 1 µm, still more preferably from 10 to 500 nm. The electron-injecting layer and the electron-transporting layer each may have a single layer structure comprising one or more of the above-described materials or may have a multi-layer structure comprising a plurality of layers which are the same or different in the composition.

The electron-injecting layer and the electron-transporting layer each is formed by a vacuum evaporation method, an LB method, an inkjet method, a method of dissolving or dispersing the above-described electron-injecting and transporting agent in a solvent and coating the solution or dispersion (e.g., spin coating, casting, dip coating) or a printing method. In the case of the coating method, the material can be dissolved or dispersed together with a resin component. Examples of the resin component include those described for the hole-injecting and transporting layer.

The material for the protective layer may be any as long as it has a function of preventing a substance which accelerates deterioration of the device, such as moisture and oxygen, from entering the device. Specific examples thereof include metals such as In, Sn, Pb, Au, Cu, Ag, Al, Ti and Ni, metal oxides such as MgO, SiO, $SiO_2$, $Al_2O_3$, GeO, NiO, CaO, BaO, $Fe_2O_3$, $Y_2O_3$ and $TiO_2$, metal fluorides such as $MgF_2$, LiF, $AlF_3$ and $CaF_2$, polyethylene, polypropylene, polymethyl methacrylate, polyimide, polyurea, polytetrafluoroethylene, polychlorotrifluoroethylene, polydichlorodifluoroethylene, a copolymer of chlorotrifluoroethylene and dichlorodifluoroethylene, a copolymer obtained by copolymerizing a monomer mixture containing tetrafluoroethylene and at least one comonomer, a fluorine-containing copolymer having a cyclic structure in the copolymer main chain, a water absorptive substance having a coefficient of water absorption of 1% or more, and a moisture-proofing substance having a coefficient of water absorption of 0.1% or less.

The method for forming the protective layer is not particularly limited and, for example, a vacuum evaporation method, a sputtering method, a reactive sputtering method, an MBE (molecular beam epitaxy) method, a cluster ion beam method, an ion plating method, a plasma polymerization method (high frequency exciting ion plating method), a plasma CVD method, a laser CVD method, a thermal CVD method, a gas source CVD method, a coating method, an inkjet method and a printing method may be used.

Preferred embodiments of the present invention are described below.

1) A compound represented by the following formula (I):

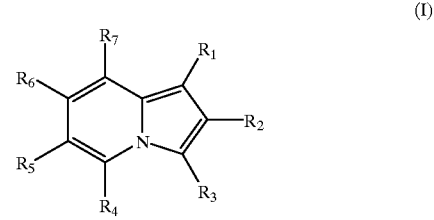

(I)

wherein $R_1$ to $R_7$ each independently represents hydrogen atom, a halogen atom, a cyano group, a formyl group, a substituted or unsubstituted alkyl group, a substituted or unsubstituted alkenyl group, a substituted or unsubstituted alkynyl group, a substituted or unsubstituted aryl group, a substituted or unsubstituted heterocyclic group, a substituted or unsubstituted primary amino group, a substituted or unsubstituted secondary amino group, a substituted or unsubstituted tertiary amino group, a substituted or unsubstituted imino group, a substituted or unsubstituted alkoxy group, a substituted or unsubstituted aryloxy group, a substituted or unsubstituted alkylthio group, a substituted or unsubstituted arylthio group, a substituted or unsubstituted carbonamido group, a substituted or unsubstituted sulfonamido group, a substituted or unsubstituted carbamoyl group, a substituted or unsubstituted sulfamoyl group, a substituted or unsubstituted alkylcarbonyl group, a substituted or unsubstituted arylcarbonyl group, a substituted or unsubstituted alkylsulfonyl group, a substituted or unsubstituted arylsulfonyl group, a substituted or unsubstituted alkoxycarbonyl group, a substituted or unsubstituted aryloxycarbonyl group, a substituted or unsubstituted alkylcarbonyloxy group, a substituted or unsubstituted arylcarbonyloxy group, a substituted or unsubstituted urethane group, a substituted or unsubstituted ureido group or a substituted or unsubstituted carboxylic acid ester group, two or more groups selected from $R_1$ to $R_7$ may combine with each other to form an aliphatic carbon ring, an aromatic carbon ring, a non-aromatic heterocyclic ring or an aromatic heterocyclic ring, and a polymer compound having the structure represented by formula (I) in a part of the repeating unit thereof may also be formed.

2) An organic light-emitting device material comprising at least one compound represented by formula (I) or a precursor thereof.

3) The organic light-emitting device material as described in Embodiment 1 or 2, which contains a polymer compound derived from a compound containing a polymerizable group in $R_1$ to $R_7$ in formula (I).

4) An organic light-emitting device comprising at least one organic light-emitting device material described in Embodiments 1 to 3.

5) The organic light-emitting device as described in Embodiment 4, wherein at least one organic layer is formed by coating.

6) A compound wherein in formula (II) or (III), R is hydrogen atom.

7) A compound wherein in formula (II) or (III), at least one of $R_{11}$ to $R_{14}$ has a substituent except for hydrogen atom.

8) A compound wherein in formula (II) or (III), at least one of $R_{11}$ to $R_{14}$ has a substituent except for hydrogen atom and being selected from the group consisting of an alkyl group, an aryl group, an alkenyl group, an alkynyl group and a heterocyclic group.

9) A compound wherein in formula (II) or (III), at least one of $R_{15}$ and $R_{16}$ has two or more benzene rings or at least one substituent selected from a condensed polycycloaromatic hydrocarbon group and a heteroaromacyclic group.

10) An organic light-emitting device material comprising at least one compound represented by formula (II) or (III).

11) An organic light-emitting device comprising at least one organic light-emitting device material comprising at least one compound represented by formula (II) or (III).

12) An organic light-emitting device comprising at least one hole-transporting layer between a pair of electrodes, wherein the hole-transporting layer contains at least one compound represented by formula (II) or (III).

13) An organic light-emitting device comprising at least one hole-injecting layer between a pair of electrodes, wherein the hole-injecting layer contains at least one compound represented by formula (II) or (III).

14) An organic light-emitting device comprising at least one electron-transporting layer between a pair of electrodes, wherein the electron-transporting layer contains at least one compound represented by formula (II) or (III).

15) An organic light-emitting device comprising at least one electron-injecting layer between a pair of electrodes, wherein the electron-injecting layer contains at least one compound represented by formula (II) or (III).

16) An organic light-emitting device comprising at least one light-emitting layer between a pair of electrodes, wherein the light-emitting layer contains at least one compound represented by formula (II) or (III).

17) The organic light-emitting device as described in Embodiments 11) to 16), wherein at least one organic layer is formed by coating.

18) An organic light-emitting device material comprising at least one compound represented by formula (V).

19) An organic light-emitting device comprising at least one organic light-emitting device material comprising at least one compound represented by formula (V).

20) An organic light-emitting device comprising at least one hole-transporting layer between a pair of electrodes, wherein the hole-transporting layer contains at least one compound represented by formula (V).

21) An organic light-emitting device comprising at least one hole-injecting layer between a pair of electrodes, wherein the hole-injecting layer contains at least one compound represented by formula (V).

22) An organic light-emitting device comprising at least one electron-transporting layer between a pair of electrodes, wherein the electron-transporting layer contains at least one compound represented by formula (V).

23) An organic light-emitting device comprising at least one electron-injecting layer between a pair of electrodes, wherein the electron-injecting layer contains at least one compound represented by formula (V).

24) An organic light-emitting device comprising at least one light-emitting layer between a pair of electrodes, wherein the light-emitting layer contains at least one compound represented by formula (V).

25) The organic light-emitting device as described in Embodiments 19) to 24), wherein at least one organic layer is formed by coating.

The present invention is described in greater detail below by referring to the Examples, however, the present invention should not be construed as being limited thereto.

EXAMPLE 1

A glass plate of 25 mm×25 mm×0.7 mm having formed thereon an ITO film to a thickness of 150 nm (produced by Tokyo Sanyo Shinku K.K.) was used as a transparent support plate. This transparent support plate was etched and washed and thereafter, copper phthlocyanine was deposited thereon to about 10 nm. Subsequently, TPD (N,N'-bis(3-methylphenyl)-N,N'-diphenylbenzidine) and Alq (tris(8-hydroxyquinolinato)aluminum) as the third layer were sequentially deposited to about 40 nm and about 60 nm, respectively, in vacuum under the conditions that the plate temperature was room temperature. On the thus-formed organic thin film, a patterned mask (a mask of giving an emission area of 5 mm×5 mm) was placed and in an evaporation unit, magnesium:silver (10:1) were co-deposited to 250 nm and then silver was deposited to 300 nm to manufacture Device 101.

EL Devices 102 to 108 having the same composition as Device 101 were manufactured except for using three kinds of Comparative Compounds and four kinds of compounds of the present invention in place of TPD of Device 101.

A d.c. constant voltage was applied to the EL device using Source Measure Unit Model 2400 manufactured by Toyo Technica and light was emitted. The luminance and the emission wavelength were measured by Luminance Meter BM-8 manufactured by Topcon KK and Spectrum Analyzer PMA-11 manufactured by Hamamatsu Photonics KK, respectively. The results are shown in Table 1 below.

TABLE 1

| Device No. | Hole-Transporting Material | Emission λmax (nm) | Luminance at Applied Voltage of 10 V (cd/m²) |
| --- | --- | --- | --- |
| 101 (Comparative Example) | TPD | 525 | 5500 |
| 102 (Comparative Example) | A | 521 | 153 |

TABLE 1-continued

| Device No. | Hole-Transporting Material | Emission λmax (nm) | Luminance at Applied Voltage of 10 V (cd/m²) |
|---|---|---|---|
| 103 (Comparative Example) | B | 525 | 257 |
| 104 (Comparative Example) | C | 524 | 275 |
| 105 (Invention) | A-HT-16 | 527 | 5600 |
| 106 (Invention) | A-HT-19 | 526 | 6020 |
| 107 (Invention) | A-HT-22 | 525 | 7500 |
| 108 (Invention) | A-HT-28 | 523 | 7100 |

Comparative Compound A

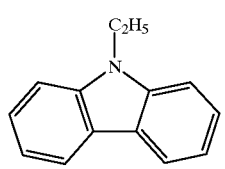

Comparative Compound B

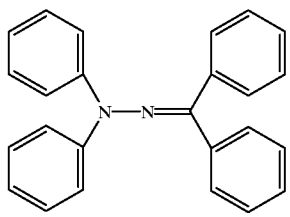

Comparative Compound C

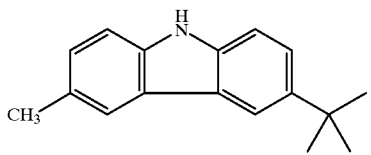

Each device was sealed in an autoclave purged with argon gas and after storage for 10 days under the heating condition of 85° C., the measurement of luminance and the observation of emission plane state were performed in the same manner. The results are shown in Table 2 below.

TABLE 2

| Device No. | Emission λmax (nm) | Luminance at Applied Voltage of 10 V (cd/m²) | Emission Plane State (evaluation with an eye) |
|---|---|---|---|
| 101 (Comparative Example) | 523 | 1470 | Poor |
| 102 (Comparative Example) | 522 | 35 | Poor |
| 103 (Comparative Example) | 524 | 107 | Poor |
| 104 (Comparative Example) | 525 | 103 | Poor |
| 105 (Invention) | 526 | 2600 | Fair |
| 106 (Invention) | 527 | 5300 | Good |

TABLE 2-continued

| Device No. | Emission λmax (nm) | Luminance at Applied Voltage of 10 V (cd/m²) | Emission Plane State (evaluation with an eye) |
|---|---|---|---|
| 107 (Invention) | 525 | 6500 | Good |
| 108 (Invention) | 524 | 6600 | Good |

As is apparent from the results in Table 1, light emitted from Devices 102 to 104 fabricated using a comparative compound was low in the luminance as compared with Device 101 as a type. On the other hand, in Devices 105 to 108 fabricated using the hole-transporting material of the present invention, light emission equal to or greater than that of the type was observed.

Furthermore, as seen from the results in Table 2, in the devices using the compound of the present invention, the durability was also superior to the performance of the type.

EXAMPLE 2

On an ITO glass plate which was etched and washed in the same manner as in Example 1, a solution having dissolved therein 40 mg of poly(N-vinylcarbazole) (PVK), 12 mg of 2,5-bis(1-naphthyl)-1,3,4-oxadiazole, 10 mg of coumarin-6 and 3 ml of 1,2-dichloroethane was spin-coated. At this time, the thickness of the organic layer was about 120 nm. Subsequently, the cathode was deposited in the same manner as in Example 1 to manufacture EL Device 201.

EL Devices 202 to 205 having the same composition as Device 201 were manufactured except for using two kinds of Comparative Compounds and two kinds of compounds of the present invention in place of PVK of Device 201.

A d.c. constant voltage was applied to the EL device using Source Measure Unit Model 2400 manufactured by Toyo Technica and light was emitted. The luminance and the emission wavelength were measured by Luminance Meter BM-8 manufactured by Topcon KK and Spectrum Analyzer PMA-11 manufactured by Hamamatsu Photonics KK, respectively. The results are shown in Table 3 below.

TABLE 3

| Device No. | Hole-Transporting Material | Emission λmax (nm) | Luminance at Applied Voltage of 18 V (cd/m²) |
|---|---|---|---|
| 201 (Comparative Example) | PVK | 518 | 2000 |
| 202 (Comparative Example) | D | 521 | 1720 |
| 203 (Comparative Example) | E | 517 | 1530 |
| 204 (Invention) | A-HT-32 | 520 | 4000 |
| 205 (Invention) | A-HT-34 | 519 | 3800 |

Comparative Compound D

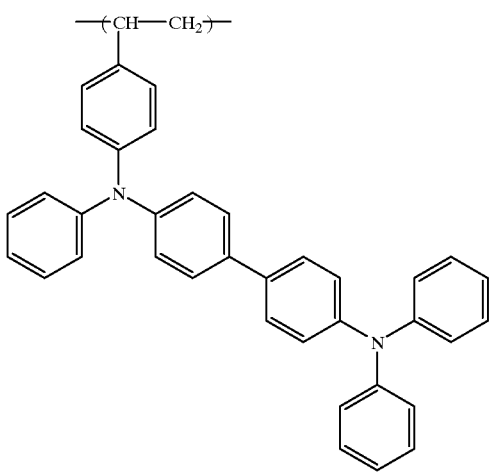

Comparative Compound E

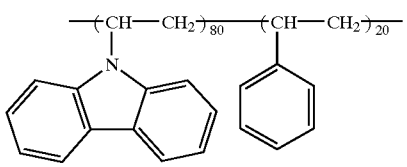

As is apparent from the results in Table 3, light emitted from Devices 202 and 203 fabricated using a comparative compound was low in the luminance as compared with Device 201 as a type. On the other hand, in Devices 204 and 205 fabricated using the hole-transporting material of the present invention, light emission equal to or greater than that of the type was observed.

EXAMPLE 3

EL Devices 302 to 310 having the same composition as Device 101 were manufactured except for using three kinds of Comparative Compounds and four kinds of compounds of the present invention in place of TPD of Device 101 in Example 1.

A d.c. constant voltage was applied to the EL device using Source Measure Unit Model 2400 manufactured by Toyo Technica and light was emitted. The luminance and the emission wavelength were measured by Luminance Meter BM-8 manufactured by Topcon KK and Spectrum Analyzer PMA-11 manufactured by Hamamatsu Photonics KK, respectively. The results are shown in Table 4 below.

TABLE 4

| Device No. | Hole-Transporting Material | Emission λmax (nm) | Luminance at Applied Voltage of 10 V (cd/m$^2$) |
|---|---|---|---|
| 101 (Comparative Example) | TPD | 525 | 5500 |
| 302 (Comparative Example) | F | 524 | 5200 |
| 303 (Comparative Example) | G | 523 | 5350 |
| 304 (Comparative Example) | H | 524 | 5550 |
| 305 (Invention) | B-HT-1 | 526 | 5600 |
| 306 (Invention) | B-HT-3 | 525 | 5650 |
| 307 (Invention) | B-HT-5 | 524 | 5450 |
| 308 (Invention) | B-HT-6 | 525 | 5450 |
| 309 (Invention) | B-HT-10 | 524 | 5500 |
| 310 (Invention) | B-HT-15 | 525 | 5600 |

Comparative Compound F

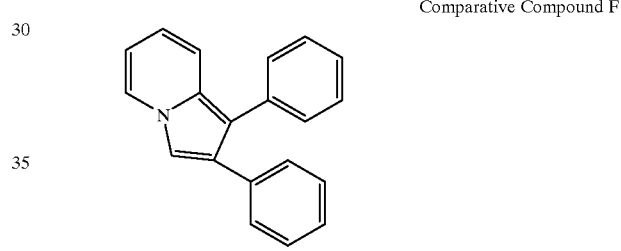

Comparative Compound G

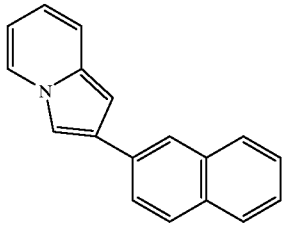

Comparative Compound H

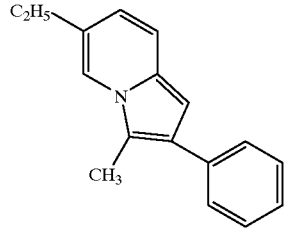

Each device was sealed in an autoclave purged with argon gas and after storage for 10 days under the heating condition of 85° C., the measurement of luminance and the observation of emission plane state were performed in the same manner. The results are shown in Table 5 below.

TABLE 5

| Device No. | Emission λmax (nm) | Luminance at Applied Voltage of 10 V (cd/m$^2$) | Emission Plate State (evaluation with an eye) |
| --- | --- | --- | --- |
| 101 (Comparative Example) | 523 | 1470 | Poor |
| 302 (Comparative Example) | 524 | 350 | Poor |
| 303 (Comparative Example) | 523 | 200 | Poor |
| 304 (Comparative Example) | 524 | 325 | Poor |
| 305 (Invention) | 525 | 5300 | Good |
| 306 (Invention) | 525 | 5400 | Good |
| 307 (Invention) | 524 | 5250 | Good |
| 308 (Invention) | 525 | 5200 | Good |
| 309 (Invention) | 526 | 5300 | Good |
| 310 (Invention) | 525 | 5450 | Good |

On comparison between the results in Table 4 and the results in Table 5, light emission observed immediately after the fabrication is equal to that of the type in all devices. On the other hand, comparison on the device performance after high-temperature aging clearly reveals that Devices 305 to 310 using the compound of the present invention are superior in the durability to the type.

EXAMPLE 4

On an ITO glass plate which was etched and washed in the same manner as in Example 1, a solution having dissolved therein 30 mg of polycarbonate, 30 mg of TPD and 3 ml of 1,2-dichloroethane was spin-coated. At this time, the thickness of the organic layer was about 60 nm. Subsequently, Alq and cathode were deposited in the same manner as in Example 1 to manufacture EL Device 401.

EL Devices 402 to 405 having the same composition as Device 401 were manufactured except for using two kinds of Comparative Compounds and two kinds of compounds of the present invention in place of TPD of Device 401.

A d.c. constant voltage was applied to the EL device using Source Measure Unit Model 2400 manufactured by Toyo Technica and light was emitted. The luminance and the emission wavelength were measured by Luminance Meter BM-8 manufactured by Topcon KK and Spectrum Analyzer PMA-11 manufactured by Hamamatsu Photonics KK, respectively. The results are shown in Table 6 below.

TABLE 6

| Device No. | Hole-Transporting Material | Emission λmax (nm) | Luminance at Applied Voltage of 18 V (cd/m$^2$) |
| --- | --- | --- | --- |
| 401 (Comparative Example) | TPD | 522 | 2550 |
| 402 (Comparative Example) | F | 521 | 2550 |
| 403 (Comparative Example) | H | 522 | 2600 |
| 404 (Invention) | B-HT-1 | 521 | 2650 |
| 405 (Invention) | B-FT-10 | 521 | 2600 |

Each device was sealed in an autoclave purged with argon gas and after storage for 10 days under the heating condition of 85° C., the measurement of luminance and the observation of emission plane state were performed in the same manner. The results are shown in Table 7 below.

TABLE 7

| Device No. | Emission λmax (nm) | Luminance at Applied Voltage of 18 V (cd/m$^2$) | Emission Plate State (evaluation with an eye) |
| --- | --- | --- | --- |
| 401 (Comparative Example) | 521 | 200 | Poor |
| 402 (Comparative Example) | 522 | 210 | Poor |
| 403 (Comparative Example) | 522 | 190 | Poor |
| 404 (Invention) | 521 | 2350 | Good |
| 405 (Invention) | 521 | 2400 | Good |

In the results shown in Table 6, luminance of all devices is equal to that of Device 401, however, from the results shown in Table 7, it is seen that Devices 404 to 405 using the compound of the present invention are superior in the durability during storage under high-temperature conditions to Comparative Devices 401 to 403. These results reveal that the compounds of the present invention are effective as compared with the comparative compounds.

EXAMPLE 5

(Synthesis of Compound INB-1)

Through a solution obtained by dissolving 959 mg (5 mmol) of 2-phenylindolizine and 3.75 ml of tetramethylethylenediamine (TMEDA) in 50 ml of waterless tetrahydrofuran (THF) for organic synthesis chemistry, a nitrogen stream was passed and while stirring, the inner temperature was kept at −40° C. or less using a dry ice bath. Thereto, 3.41 ml (5.5 mmol) of a 1.6N n-butyllithiumhexane solution was added dropwise while taking care not to allow the inner temperature to exceed −40° C. After the completion of dropwise addition, stirring was continued for 3 hours under the same temperature condition. To the resulting reaction mixture, 1,395 mg (7.5 mmol) of 2-isopropoxy-4,4,5,5-tetramethyl-1,3,2-dioxaborane was added dropwise and stirring was continued at that temperature for 2 hours. Thereafter, the dry ice bath was removed and the stirring was further continued until the condition reached room temperature. The reaction mixture was poured into ether/aqueous 0.1N ammonium chloride solution and subjected to a liquid separation operation. Thereafter, the ether phase was further subjected to a liquid separation operation with water. After removing the aqueous phase, the ether phase was dried over anhydrous sodium sulfate and the solvent was distilled off under reduced pressure. To the oily compound obtained, acetonitrile was added and the mixture was heated and then cooled, as a result, crystals were precipitated. The crystals were separated by filtration and dried to obtain 1,022 mg of crystals of INB-1.

(Synthesis of Compound C-HT-10)

In 20 ml of diethylene glycol dimethyl ether, 3.02 g (10 mmol) of Compound INB-1 and 944 mg (3 mmol) of 1,3,5-tribromobenzene were dissolved and thereto, 1 ml of water, 2.12 g (20 mmol) of sodium carbonate, a catalytic amount of Pd—Carbon (Pd: 5%) and triphenylphosphine were added and refluxed for 5 hours. With the progress of reaction, the product was produced as crystals. After the reaction, the reaction mixed solution was added to a chloroform/water mixed solvent and after thorough stirring, the solution was filtered through Celite. The chloroform phase of the filtrate was liquid-separated and further liquid-separated with water. Thereafter, the chloroform phase was dried over anhydrous sodium sulfate and the solvent was distilled off under reduced pressure. The crystals obtained were recrystallized from a THF-methanol mixed solvent to obtain 2.7 g of crystals of Compound C-HT-10.

(Evaluation 1 as Organic Light-Emitting Device Material)

EL Devices 502 to 508 having the same composition as Device 101 were manufactured except for using seven kinds of compounds of the present invention in place of TPD of Device 101 in Example 1.

A d.c. constant voltage was applied to the EL device using Source Measure Unit Model 2400 manufactured by Toyo Technica and light was emitted. The luminance and the emission wavelength were measured by Luminance Meter BM-8 manufactured by Topcon KK and Spectrum Analyzer PMA-11 manufactured by Hamamatsu Photonics KK, respectively. The results are shown in Table 8 below.

TABLE 8

| Device No. | Hole-Transporting Material | Emission λmax (nm) | Luminance at Applied Voltage of 10 V (cd/m$^2$) |
|---|---|---|---|
| 101 (Comparative Example) | TPD | 525 | 5500 |
| 502 (Invention) | C-HT-1 | 523 | 5600 |
| 503 (Invention) | C-HT-3 | 525 | 5550 |
| 504 (Invention) | C-HT-6 | 525 | 5550 |
| 505 (Invention) | C-HT-8 | 524 | 5450 |
| 506 (Invention) | C-HT-10 | 526 | 5400 |
| 507 (Invention) | C-HT-15 | 525 | 5350 |
| 508 (Invention) | C-HT-19 | 524 | 5600 |

As is apparent from the results in Table 8, in Devices 502 to 508 using the compound of the present invention, light emission equal to that of the type was also observed.

Evaluation 2 as Organic Light-Emitting Device Material)

EL Devices 602 to 605 having the same composition as Device 401 were manufactured except for using four kinds of compounds of the present invention in place of TPD of Device 401 in Example 4.

A d.c. constant voltage was applied to the EL device using Source Measure Unit Model 2400 manufactured by Toyo Technica and light was emitted. The luminance and the emission wavelength were measured by Luminance Meter BM-8 manufactured by Topcon KK and Spectrum Analyzer PMA-11 manufactured by Hamamatsu Photonics KK, respectively. The results are shown in Table 9 below.

TABLE 9

| Device No. | Hole-Transporting Material | Emission λmax (nm) | Luminance at Applied Voltage of 10 V (cd/m$^2$) |
|---|---|---|---|
| 401 (Comparative Example) | TPD | 522 | 2550 |
| 602 (Invention) | C-HT-1 | 521 | 2400 |
| 503 (Invention) | C-HT-6 | 522 | 2500 |
| 604 (Invention) | C-HT-8 | 522 | 2500 |
| 605 (Invention) | C-HT-15 | 521 | 2450 |

As is apparent from the results in Table 9, in Devices 602 to 605 using the compound of the present invention, light emission equal to that of the type was also observed.

By using the indolizine compound of the present invention, a light-emitting device favored with high luminance, excellent durability in the storage under high-temperature conditions and good emission plane state can be obtained.

Furthermore, by using the 5-substituted indolizine compound of the present invention, an organic light-emitting device ensuring high luminance can be obtained.

While the invention has been described in detail and with reference to specific embodiments thereof, it will be apparent to one skilled in the art that various changes and modifications can be made therein without departing from the spirit and scope thereof.

What is claimed is:

1. An organic light-emitting device material comprising at least one compound represented by formula (I) or a precursor thereof:

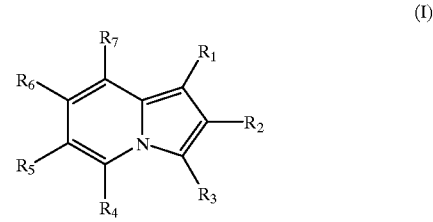

(I)

wherein $R_1$ to $R_7$ each independently represents hydrogen atom, a halogen atom, a cyano group, a formyl group, a substituted or unsubstituted alkyl group, a substituted or unsubstituted alkenyl group, a substituted or unsubstituted alkynyl group, a substituted or unsubstituted aryl group, a substituted or unsubstituted heterocyclic group, a substituted or unsubstituted primary amino group, a substituted or unsubstituted secondary amino group, a substituted or unsubstituted tertiary amino group, a substituted or unsubstituted imino group, a substituted or unsubstituted alkoxy group, a substituted or unsubstituted aryloxy group, a substituted or unsubstituted alkylthio group, a substituted or unsubstituted arylthio group, a substituted or unsubstituted carbonamido group, a substituted or unsubstituted sulfonamido group, a substituted or unsubstituted carbamoyl group, a substituted or unsubstituted sulfamoyl group, a substituted or unsubstituted alkylcarbonyl group, a substituted or unsubstituted arylcarbonyl group, a substituted or unsubstituted alkyl-sulfonyl group, a substituted or unsubstituted arylsulfonyl group, a substituted or unsubstituted alkoxycarbonyl group, a substituted or unsubstituted aryloxycarbonyl group, a substituted or unsubstituted alkylcarbonyloxy group, a substituted or unsubstituted arylcarbonyloxy group, a substituted or unsubstituted urethane group, a substituted or unsubstituted ureido group or a substituted or unsubstituted carboxylic acid ester group, two or more groups selected from $R_1$ to $R_7$ may combine with each other to form an aliphatic carbon ring, an aromatic carbon ring, a non-aromatic heterocyclic ring or an aromatic heterocyclic ring and $R_4$ may further represent

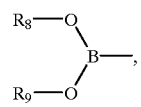

$R_8$ and $R_9$ each represents hydrogen atom, an alkyl group, an aryl group or a heterocyclic group, $R_8$ and $R_9$ may combine with each other to form a cyclic structure or may form a polymer compound having the structure represented by formula (I) in a part of the repeating unit thereof and R₁ or R₃ in the structure represented by formula (I) and

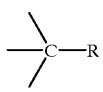

may combine to form a trimer compound, and R represents hydrogen atom, an alkyl group, an aryl group or a heterocyclic group.

2. The organic light-emitting device material as claimed in claim 1, which contains a polymer compound derived from a compound containing a polymerizable group in $R_1$ to $R_7$ of formula (I), a trimer compound formed resulting from the combining of $R_1$ or $R_3$ in formula (I) and

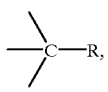

or a compound in which $R_4$ in formula (I) is

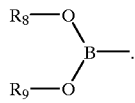

3. A method for producing a compound represented by the following formula (V), comprising coupling a compound represented by the following formula (IV) with a vinyl halide, aryl halide or heteroaryl halide compound using a palladium catalyst:

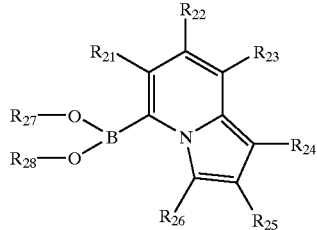

(IV)

wherein $R_{21}$ to $R_{26}$ each independently represents a substituent selected from the group consisting of hydrogen atom, a substituted or unsubstituted alkyl group, a substituted or unsubstituted alkenyl group, a substituted or unsubstituted alkynyl group, a substituted or unsubstituted aryl group, a substituted or unsubstituted heterocyclic group, a substituted or unsubstituted alkoxy group, a substituted or unsubstituted aryloxy group, a substituted or unsubstituted alkylthio group, a substituted or unsubstituted arylthio group, a substituted or unsubstituted alkylamino group, a substituted or unsubstituted arylamino group, a substituted or unsubstituted alkylcarbonyl group, a substituted or unsubstituted arylcarbonyl group, a substituted or unsubstituted alkylsulfonyl group, a substituted or unsubstituted arylsulfonyl group, a substituted or unsubstituted alkoxycarbonyl group, a substituted or unsubstituted aryloxycarbonyl group, a substituted or unsubstituted alkylcarbamoyl group, a substituted or unsubstituted arylcarbamoyl group, a substituted or unsubstituted alkylsulfamoyl group, a substituted or unsubstituted arylsulfamoyl group, a substituted or unsubstituted alkylcarbonyloxy group, a substituted or unsubstituted arylcarbonyloxy group, a substituted or unsubstituted alkylcarbonamido group, a substituted or unsubstituted arylcarbonamido group, a substituted or unsubstituted alkylsulfonamido group, a substituted or unsubstituted arylsulfonamido group, a substituted or unsubstituted urethane group, a substituted or unsubstituted ureido group and a substituted or unsubstituted carbonic acid ester group, the substituents selected from $R_{21}$ to $R_{26}$ may combine with each other to form a cyclic structure, $R_{27}$ and $R_{28}$ each represents hydrogen atom, an alkyl group, an aryl group or a heterocyclic group, and $R_{27}$ and $R_{28}$ may combine with each other to form a cyclic structure,

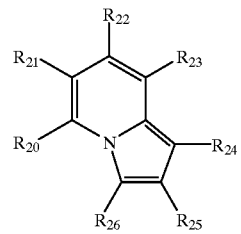

(V)

wherein $R_{20}$ represents an alkenyl group, an aryl group or a heteroaryl group, and $R_{21}$ to $R_{26}$ are the same as the substituent described in formula (IV).

4. An organic light-emitting device having at least one organic light-emitting device material comprising at least one compound represented by formula (I) or a precursor thereof:

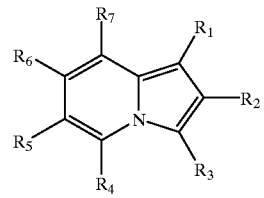

(I)

wherein $R_1$ to $R_7$ each independently represents hydrogen atom, a halogen atom, a cyano group, a formyl group, a substituted or unsubstituted alkyl group, a substituted or unsubstituted alkenyl group, a substituted or unsubstituted alkynyl group, a substituted or unsubstituted aryl group, a substituted or unsubstituted heterocyclic group, a substituted or unsubstituted primary amino group, a substituted or unsubstituted secondary amino group, a substituted or unsubstituted tertiary amino group, a substituted or unsubstituted imino group, a substituted or unsubstituted alkoxy group, a substituted or unsubstituted aryloxy group, a substituted or unsubstituted alkylthio group, a substituted or unsubstituted arylthio group, a substituted or unsubstituted carbonamido group, a substituted or unsubstituted sulfonamido group, a substituted or unsubstituted carbamoyl group, a substituted or unsubstituted sulfamoyl group, a substituted or unsubstituted alkylcarbonyl group, a substituted or unsubstituted arylcarbonyl group, a substituted or unsubstituted alkylsulfonyl group, a substituted or unsubstituted arylsulfonyl group, a substituted or unsubstituted alkoxycarbonyl group, a substituted or unsubstituted aryloxycarbonyl group, a substituted or unsubstituted alkylcarbonyloxy group, a substituted or unsubstituted arylcarbonyloxy group, a substituted or unsubstituted urethane group, a substituted or unsubstituted ureido group or a substituted or unsubstituted carboxylic acid ester group, two or more groups selected from $R_1$ to $R_7$ may combine with each other to form an aliphatic carbon ring, an aromatic carbon ring, a non-aromatic heterocyclic ring or an aromatic heterocyclic ring and $R_4$ may further represent

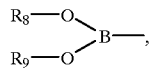

$R_8$ and $R_9$ each represents hydrogen atom, an alkyl group, an aryl group or a heterocyclic group, $R_8$ and $R_9$ may combine with each other to form a cyclic structure or may form a polymer compound having the structure represented by formula (I) in a part of the repeating unit thereof and $R_1$ or $R_3$ in the structure represented by formula (I) and

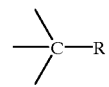

may combine to form a trimer compound, and R represents hydrogen atom, an alkyl group, an aryl group or a heterocyclic group.

5. The organic light-emitting device as claimed in claim 4, wherein at least one organic layer is formed by coating.

* * * * *